(12) United States Patent
Richman

(10) Patent No.: US 7,705,988 B2
(45) Date of Patent: Apr. 27, 2010

(54) GAS DETECTION

(75) Inventor: Lee P Richman, Wareham (GB)

(73) Assignee: Senscient Limited, Dorset (GB)

( * ) Notice: Subject to any disclaimer, the term of this patent is extended or adjusted under 35 U.S.C. 154(b) by 542 days.

(21) Appl. No.: 10/592,473

(22) PCT Filed: Mar. 8, 2005

(86) PCT No.: PCT/GB2005/000876

§ 371 (c)(1),
(2), (4) Date: Sep. 11, 2006

(87) PCT Pub. No.: WO2005/088275

PCT Pub. Date: Sep. 22, 2005

(65) Prior Publication Data

US 2007/0131882 A1 Jun. 14, 2007

(30) Foreign Application Priority Data

| Mar. 9, 2004 | (GB) | 0405252.8 |
| Mar. 24, 2004 | (GB) | 0406559.5 |
| Apr. 2, 2004 | (GB) | 0407533.9 |
| Sep. 27, 2004 | (GB) | 0421319.5 |

(51) Int. Cl.
*G01N 21/00* (2006.01)

(52) U.S. Cl. ..................... 356/437; 356/432

(58) Field of Classification Search ......... 356/300–334, 356/402–425, 450–458
See application file for complete search history.

(56) References Cited

U.S. PATENT DOCUMENTS 3,700,890 A * 10/1972 Kruezer ............. 250/341.1
3,805,074 A 4/1974 McCormack
3,846,716 A * 11/1974 Dyatlov et al. ......... 372/29.021

(Continued)

FOREIGN PATENT DOCUMENTS

EP 0 364 642 4/1990

(Continued)

OTHER PUBLICATIONS

UK Search Report dated Jul. 13, 2004 in Patent Application No. GB0406559.5.

(Continued)

*Primary Examiner*—Gregory J Toatley, Jr.
*Assistant Examiner*—Jarreas C. Underwood
(74) *Attorney, Agent, or Firm*—Nixon & Vanderhye PC

(57) ABSTRACT

Apparatus for detecting a target gas in a monitored space includes two laser diodes driven by drive circuits at electrical frequencies f and f' that are not harmonically related. The lasers operate at mean wavelengths $\Lambda_1$ and $\Lambda_2$ respectively close to two different absorption lines of the target gas and are scanned over wavelength ranges $\partial\Lambda_1$ and $\partial\Lambda_2$ respectively. The outputs from the lasers are collimated by an optical element and delivered to a receiver element after passing through the space. The receiver element focuses the radiation from both lasers onto a detector where the optical signals are combined into a single electrical signal with principal frequency components f and f'. A quantity of target gas $Q_1$ is calculated from the amplitude of frequency component $f_1$ for measurements made around wavelength $\Lambda_1$ and a quantity of target gas $Q_2$ is calculated from the amplitude of frequency component $f_2$ for measurements made around wavelength $\Lambda_2$.

92 Claims, 15 Drawing Sheets

U.S. PATENT DOCUMENTS

| | | | | |
|---|---|---|---|---|
| 3,995,960 | A * | 12/1976 | Fletcher et al. | 356/433 |
| 4,493,553 | A * | 1/1985 | Korb et al. | 356/43 |
| 4,535,241 | A * | 8/1985 | Eberhardt | 250/339.13 |
| 4,733,084 | A | 3/1988 | Oosaka | |
| 4,849,637 | A * | 7/1989 | Cerff et al. | 250/345 |
| 4,918,700 | A * | 4/1990 | Gambini | 372/32 |
| 5,002,391 | A * | 3/1991 | Wolfrum et al. | 356/307 |
| 5,267,019 | A | 11/1993 | Whittaker et al. | |
| 5,301,014 | A | 4/1994 | Koch | |
| 5,317,156 | A * | 5/1994 | Cooper et al. | 250/345 |
| 5,321,970 | A | 6/1994 | Davies et al. | |
| 5,543,621 | A | 8/1996 | Sauke et al. | |
| 5,969,825 | A | 10/1999 | Bomse et al. | |
| 6,064,488 | A | 5/2000 | Brand et al. | |
| 6,274,879 | B1 | 8/2001 | Best-Timmann | |
| 6,455,854 | B1 | 9/2002 | Richman et al. | |
| 7,009,170 | B2 * | 3/2006 | Dobbs et al. | 250/226 |

FOREIGN PATENT DOCUMENTS

| | | |
|---|---|---|
| EP | 0 629 851 A | 12/1994 |
| EP | 1 103 804 A1 | 5/2001 |
| EP | 1 111 369 A1 | 6/2001 |

OTHER PUBLICATIONS

UK Search Report dated Jun. 30, 2004 in Patent Application No. GB0407533.9.

UK Search Report dated Jun. 30, 2004 in Patent Application No. GB0405252.8.

UK Search Report dated Jun. 16, 2005 in Patent Application No. GB0421319.5.

Frish et al, "Handheld Laser-Based Sensor for Remote Detection of Toxic and Hazardous Gases", SPIE Paper No. 4199-05, 2000, pp. 1-10, XP002330267.

Schilt et al., "Wavelength modulation spectroscopy: combined frequency and intensity laser modulation", Applied Optics, vol. 42, No. 33, Nov. 20, 2003, pp. 6728-6738, XP002330268, p. 6734.

Fernholz et al., "Digital, phase-sensitive detection for in situ diode-laser spectroscopy under rapidly changing transmission conditions", Appl. Phys. B, vol. 75, Sep. 12, 2002, pp. 229-236, XP002330406.

Gabrysch et al., "Simultaneous detection of CO and CO2 using a semiconductor DFB Diode laser at 1.578 MUM", Applied Physics B: Lasers and Optics, vol. B65, No. 1, Jul. 1997, pp. 75-79, XP000658715.

Bomse et al., "Frequency Modulation and Wavelength Modulation Spectroscopies: Comparison of Experimental Methods using a Lead-Salt Diode Laser", Applied Optics, Optical Society of America, vol. 31, No. 6, Feb. 10, 1992, pp. 718-731, XP000248586.

Weldon et al., "H2S and CO2 gas sensing using DFB laser diodes emitting at 1.57 mum", Sensors and Actuators B, vol. 29, No. 1, Oct. 1995, pp. 101-107, XP004000858.

Frish et al., "Handheld Laser-based sensor for remote detection of toxic and hazardous gases," SPIE Paepr No. 4199-05, p. 1-10, 2000, XP002330267.

Schilt et al., "Wavelength modulation spectroscopy: combined frequency and intensity laser modulation," Applied Optics, vol. 42, No. 33, 2003, XP002330268.

Fernholz et al., "Digital phse-sensitive detecdtion for in situ diode-laser spectroscopy under rapidly changing transmission conditions," Appl. Phys. B, vol. 75, 2002, XP002330406.

Gabrysch et al., "Simultaneous detection of CO and $CO_2$ using a semiconducxtor DFB diode laser at 1.578µm," Appl. Phys. B: Lasers and Optics, Springer Intl., Berlin, DE, vol. B65, No. 1, 1997, XP000658715.

Bomse et al., "Frequency modulation and wavelength modulation specdtroscopies: comparison of experimental methods using a lead-salt diode laser," Appied Optics, Opt. Soc. Am., vol. 31, No. 6, 1992, XP000248586.

Weldon et al., "$H_2$s and $CO_2$ gas sensing using DFB laser diodes emitting at 1.57 µm," Sensors and Actuators B, vol. 29, No. 1, p. 101-107, 1995, XP004000858.

* cited by examiner

GAS DETECTION

This application is the U.S. national phase of international application PCT/GB2005/000876, filed 8 Mar. 2005, which designated the U.S. and claims priority of GB 0405252.8, filed 9 Mar. 2004; GB 0406559.5, filed 24 Mar. 2004; GB 0407533.9, filed 2 Apr. 2004; and GB 0421319.5, filed 27 Sep. 2004, the entire contents of each of which are hereby incorporated by reference.

BACKGROUND

1. Technical Field

This invention concerns the detection of gas particularly but not necessarily exclusively the detection of toxic, flammable or otherwise hazardous gas in a work area such as a petrochemical facility.

2. Related Art

A well known way of detecting a gas is by means of laser diode spectroscopy (LDS). The output wavelength of a laser diode depends upon the applied drive current, so by selectively varying the drive current the output wavelength can be made to scan over an optical absorption line of a target gas to be detected or measured. If the output from such a laser diode is transmitted through a gas sample and focussed onto a suitable optical detector, the signal received by the detector corresponds to the product of the laser's output waveform and the transmission spectrum of the gas sample being illuminated. Then the quantity of target gas in the transmission path through the sample can be determined by measuring the change in received intensity when the laser's wavelength corresponds to the wavelength of the optical absorption line of the target gas. The amount of absorption produced by a given quantity of gas can be determined using Beer's law, $I=I_0 \cdot e^{-\sigma n}$, where $I$ is the received intensity at the detector, $I_0$ is the intensity incident upon the sample being illuminated, $\sigma$ is the absorption cross section of the target gas at the absorption wavelength and $n$ is the total number of target gas molecules in the measurement path.

LDS is widely used in applications requiring high sensitivity—in instrumentation for chemical processes, for instance, and in monitoring atmospheric pollutants. Hitherto, however, LDS has been little used in safety-related applications. The main reason for this is that such applications demand an extremely high level of reliability and in particular very low false alarm rates. Conventional LDS is sufficiently reliable to detect fractional absorbances as low as $1 \times 10^{-5}$ in process control or atmospheric monitoring applications, but such small fractional absorbances cannot be detected with an acceptably low false alarm rate for safety applications. In short, the probability of false alarms is considered too high for LDS to be used for applications such as the detection of toxic and flammable gases for which it would otherwise be suitable.

BRIEF SUMMARY

It is a first object of the present invention to enable LDS to be used satisfactorily in the detection of toxic and flammable gases and other safety applications—that is, with high sensitivity gas detection reliably but without triggering false alarms. This requires (a) reliable detection of fractional absorbances as low as $1 \times 10^{-4}$ to $1 \times 10^{-5}$ while (b) operating over open measurement paths of 5 to 100 meters length in (c) environments typical of those found at petrochemical installations, requiring the equipment to endure extreme weather and temperatures, objects moving through the monitored space, contamination building up on exposed optical surfaces and high levels of electromagnetic interference. To achieve this, it is necessary to overcome three key problems (namely, system noise, absorption by atmospheric gases and coherence/fringe effects) and, in the present exemplary embodiment, this is achieved by driving the laser diode alternately at two selected wavelengths—what for convenience is referred to herein as "dual wavelength LDS".

Thus, according to a first aspect of the exemplary embodiment, there is provided a method of detecting a target gas in a monitored space comprising applying an electrical control current to a laser diode so as to generate optical radiation of a wavelength defined by the control current, transmitting the optical radiation across the monitored space and determining the optical absorption thereof, characterized in that the control current defines two mean wavelengths $\Lambda_1$ and $\Lambda_2$ for the optical radiation and includes electrical modulation at two frequencies f and f', wherein $\Lambda_1$ and $\Lambda_2$ are respectively close (as hereinafter defined) to two separate optical absorption lines of the target gas and f and f' are not harmonically related.

The term "close" as used above in relation to $\Lambda_1$ and $\Lambda_2$ means that the modulation of the control current is sufficient to shift the optical radiation at least to the corresponding optical absorption line. In other words, wavelength $\Lambda_1$ is close enough to one optical absorption line for modulation at frequency f to create a cyclical variation in the wavelength of the optical radiation sufficient to scan over part or all of that absorption line, and similarly $\Lambda_2$ and the modulation at f' are such that the cyclical wavelength variation created scans over part or all of the other optical absorption line.

It may be noted here that the cyclical variation in the frequency of the optical radiation is much larger (typically many GHz) than the electrical modulation frequency. Thus, modulation at a relatively low electrical frequency is used to move the frequency of the optical radiation back and forth by many GHz to scan over the absorption line of the target gas. At the same time, because the electrical modulation frequency is very low compared with the frequency of the optical radiation, any optical sidebands generated by the electrical modulation, which might otherwise be troublesome, will be too close to the mean frequency of the optical radiation to be resolved.

For the avoidance of doubt, this mode of operation should not be confused with that in which the drive current of a laser diode is electrically modulated at high frequency (multi-GHz) deliberately to generate optical sidebands that are then used to probe an absorption line.

The optical radiation may be generated from a single laser diode and the control current comprise a bias component which is alternated between two values respectively defining $\Lambda_1$ and $\Lambda_2$. Alternatively the optical radiation may be generated from two laser diodes of which one has a said control current comprising a bias component of value defining $\Lambda_1$ and the other has a said control current comprising a bias component defining $\Lambda 2$.

The electrical modulation applied to the or each laser diode is preferably sinusoidal.

According to a second aspect of the exemplary embodiment, there is provided apparatus for detecting a target gas in a monitored space, which apparatus comprises a laser diode operable to transmit radiation across the monitored space and a first optical receiver operable to receive the transmitted radiation and determine optical absorption thereof, characterized in that a control current is applied to the laser diode to define two mean wavelengths $\Lambda_1$ and $\Lambda_2$ for the optical radiation and is electrically modulated at two frequencies f and f', wherein $\Lambda_1$ and $\Lambda_2$ are respectively close (as hereinbefore defined) to two separate optical absorption lines of the target gas and f and f' are not harmonically related.

The apparatus may comprise a single laser diode with the control current applied thereto comprising a bias component alternated between two values respectively defining $\Lambda_1$ and $\Lambda_2$ or it may comprise two laser diodes of which one has a control current comprising a bias component defining $\Lambda_1$ and the other has a control current comprising a bias component defining $\Lambda_2$. In each arrangement the electrical modulation is preferably sinusoidal.

In another aspect, apparatus according to the exemplary embodiment may comprise a laser diode driven by a current comprising two components, a bias component and a sinusoidal component, the bias component alternating between two levels chosen to operate the laser diode at two mean wavelengths $\Lambda_1$ and $\Lambda_2$, close to two separate optical absorption lines of the same target gas, the sinusoidal component synchronously alternating between two, non-harmonically related electrical frequencies f and F' at which the laser's wavelength is scanned across one or the other of the chosen absorption lines for a prescribed interval, the optical radiation from the laser diode being collected and transmitted through the monitored space and subsequently illuminating an optical detector, the electrical signal from this optical detector being amplified, digitized and processed to determine the magnitudes of frequency components f, f', $f_1$ and $f_2$, where frequencies $f_1$, and $f_2$ are similar order harmonics of the non-harmonically related electrical frequencies f and f', normalization of the magnitudes of $f_1$ and $f_2$ with respect to their fundamentals, calculation of quantities $Q_1$ and $Q_2$, separate estimates of the amount of target gas in the monitored space based upon the normalized magnitude of frequency components $f_1$ and $f_2$, comparison of quantities $Q_1$ and $Q_2$ to determine the quality of their agreement with each other and previous results for measurements made through the monitored space; and applying rules dependent upon this quality, use of $Q_1$ and $Q_2$ in combination with previous results to calculate the quantity of target gas present in the monitored space, this calculated quantity of gas being output by the apparatus using conventional means.

Such apparatus may comprise two or more laser diodes, each laser diode being driven by a bias current which causes it to operate at a mean wavelength close to a different optical absorption line of the same target gas and being scanned across this line by a sinusoidal current component at a frequency which is non-harmonically related to any other scanning frequency used, the optical radiation from all laser diodes being collected and transmitted through the monitored space and subsequently illuminating one or more optical detectors, the electrical signal from the detector or detectors being amplified, digitized and processed to determine the magnitude of components at the fundamental scanning frequencies and similar order harmonics of these fundamental frequencies, normalization of each harmonic with respect to the magnitude of its fundamental, calculation of separate estimates of the quantity of target gas present in the monitored space based upon each normalized harmonic, comparison of these quantity estimates with each other and previous results for measurements made through the monitored space and applying rules dependent upon this quality, use of these quantities in combination with previous results to calculate the quantity of target gas present in the monitored space, this calculated quantity of gas being output by the apparatus using conventional means.

Preferably the wavelength scanning ranges for the laser diode(s) are non-harmonically related and have significantly different characteristic distances with respect to the formation of coherent interference fringes.

Where two laser diodes are employed, they are preferably located in positions calculated to minimise formation of coherent interference fringes with common phase, amplitude or frequency. Preferably also the radiation from each laser diode is collected and collimated by separate optical elements with different, non-harmonically related effective focal lengths and thicknesses.

Each target gas absorption line may be scanned at two, non-harmonically related electrical frequencies and measurements of any absorption by such lines made by determining the magnitude of the two, similar order harmonics of the non-harmonically related scanning frequencies, this process being carried out for each absorption line being scanned and where this process is performed simultaneously, all electrical scanning frequencies being chosen to be non-harmonically related.

The invention is of particular benefit during the extraction, transportation and processing of oil and gas, when it is necessary to protect employees and facilities from dangerous releases of flammable or toxic gases. The main flammable gas hazard encountered by the petrochemical industry is associated with the natural gas that is found at virtually all of its fields and facilities. In addition to natural gas, the petrochemical industry also uses or produces a number of other flammable gases including liquid petroleum gas (LPG), ethylene and propylene. The main toxic gas hazard encountered by the petrochemical industry is associated with hydrogen sulphide, a highly toxic, corrosive gas that is present in the oil or gas of so-called "sour" fields and facilities processing the output from sour fields. Equipment for the detection of leaking flammable or toxic gases at petrochemical facilities has been developed using a number of technologies, including catalytic, electrochemical, ultrasonic and infrared. However, despite the variety of gas detectors available and considerable efforts upon the part of their developers and the petrochemical industry to perfect them and their use, a high proportion of flammable or toxic gas leaks at petrochemical facilities go undetected or are detected too late. An ideal hazardous gas detector for the petrochemical industry would be a single gas detector capable of detecting any flammable or toxic gas that is likely to be found at its facilities with sufficient sensitivity to provide a warning before a dangerous condition is reached. In order to approach this ideal, such a detector would need to be able to detect methane, ethane, propane and butane (the main constituents of natural gas and LPG), ethylene and propylene (gases widely produced and used by the downstream petrochemical industry) and hydrogen sulphide (found in sour oil or gas).

Furthermore, such a detector would need to be able to reliably detect these gases at parts-per-million levels, in order to ensure that leaks were detected early.

It is, therefore, a further object of the present exemplary embodiment to provide a hazardous gas detector substantially conforming to the above criteria.

To this end, apparatus according to the exemplary embodiment may be configured and arranged for the detection of methane, ethane, propane or ethylene in a monitored space, wherein said bias component varies in a manner determined to operate the laser diode at wavelengths suitable for scanning either of methane's absorption lines at 1684 nm and 1687.3 nm; and one or more of the other gases' absorption lines or features at 1684.3 nm, 1686.4 nm and 1687.0 nm, and said scanning component repetitively scans the laser diode's wavelength over the chosen absorption lines or features, the optical radiation from the laser diode being collected and transmitted through the monitored space and subsequently illuminating an optical detector, the electrical signal from this optical detector being processed to determine the gas or gases present in the monitored space and the amounts of each gas present, this information being output by the detector.

Having determined the amount of methane gas present in the monitored space, the apparatus may be arranged to estimate the amount of hydrogen sulphide present in the monitored space; using a coefficient relating the amount of methane to the amount of hydrogen sulphide for the solution gas of a particular field or facility, this estimate being output by the detector.

In detecting methane gas and estimating the amount of hydrogen sulphide gas present in the monitored space, the amount of methane gas present in the monitored space may be determined using a coefficient relating the amount of methane to the amount of hydrogen sulphide for the solution gas of a particular field or facility.

Those skilled in the science will appreciate that a hazardous gas detector as above can readily provide warnings about both the flammable and toxic gas hazards presented by a leak of the solution gas from a particular, known oil or gas field. However, it relies for its operation upon knowledge of the ratio of hydrogen sulphide to methane in the solution gas that is detecting. Facilities that receive and process oil or gas from a number of different sources will not have a single, known ratio of hydrogen sulphide to methane for the solution gas. Indeed, some of the oil or gas handled by such facilities may be sweet, there being no hydrogen sulphide in the solution gas.

It is a further object of the present exemplary embodiment to enable reliable detection of hazardous gas at facilities handling oil or gas from a variety of sources.

To meet this object, apparatus according to the exemplary embodiment may comprise two laser diodes, one operated at wavelengths to scan absorption lines of flammable gases including methane, ethane and propane, the other operated at a wavelength to scan an absorption line of hydrogen sulphide.

Such apparatus preferably comprises an alarm actuated only when the apparatus detects both hydrogen sulphide and methane. The alarm may be actuated only when the detection apparatus detects methane above a predetermined threshold level. The threshold level may be determined from records of the sourness of petrochemicals handled at the facility.

Detection or measurement of gases such as methane at flammable concentrations is sufficiently easy using laser diode spectroscopy techniques that it can be performed reliably using a single laser diode. However, for reasons discussed hereinbefore the detection or measurement of hydrogen sulphide at toxic concentrations cannot be performed reliably using a single measurement, because the false alarm rate would be unacceptably high. The invention achieves an acceptably low false alarm rate for the reliable detection of hydrogen sulphide by making use of both the hydrogen sulphide measurement and the methane measurement. If sour solution gas is leaking then the hydrogen sulphide will be detected by absorption measurements made at the chosen hydrogen sulphide absorption line wavelength and methane will be detected by absorption measurements made at the chosen methane absorption line wavelength. Only if hydrogen sulphide and methane are both detected at sufficient concentrations can there genuinely be a toxic gas hazard present due to hydrogen sulphide. If the amount of methane measured in the monitored path is less than that which would be known to be present in the most sour solution gas that a particular facility might handle, then the hydrogen sulphide measurement must be false, and no toxic gas alarm should be signalled. The false alarm rejection strategy of the claimed invention is based upon the fact that whilst it is possible for solution gas to contain or not to contain hydrogen sulphide (depending upon its source) solution gas always contains a very significant quantity of methane.

European standard EN61508 defines the Safety Integrity Level (SIL) appropriate for systems used to provide protection of people from safety hazards. Where such hazards are associated with the work place, governmental safety organisations are increasingly requiring employers to deploy safety protective systems meeting an appropriate SIL level. Equipment for the detection of toxic or flammable gases can form part of a safety protective system and consequently it is desirable for such equipment to be suitable for use in systems meeting SIL levels appropriate to such applications. Previous equipment for the detection of leaking toxic or flammable gases has used a variety of technologies, including catalytic, electrochemical, semi-conductor film and infrared. However, despite the variety of gas detectors and technologies available, the majority of gas detectors currently available do not meet even the lowest SIL level (SIL 1), let alone the SIL levels considered appropriate for most industrial or petrochemical gas detection applications (SIL 2 or SIL 3).

With regard to safety integrity, the main problem with many of the currently available gas detectors is unrevealed failure of the gas sensing element. Catalytic, electrochemical and semi-conductor film based gas detectors rely upon direct chemical or physical interaction between the gas sensing element and the target gas or gases which they detect. This physical or chemical interaction takes place on surfaces which have been carefully prepared to facilitate a desired interaction with the target gas. When these surfaces are in their originally prepared condition, the gas sensing element operates as intended, but if these surfaces change during operational use, the properties on which the gas sensing element depends may become degraded or even completely lost. Unfortunately, catalytic, electrochemical and semi-conductor film gas sensors can suffer a degradation or loss of necessary surface properties as a result of exposure to a number of agents present in the atmosphere in which such gas detectors are required to operate. This problem is exacerbated by the fact that in many instances, the degradation or loss of the surface properties necessary for detection of gas is not accompanied by any discernible change in the output from the sensing element in the normal, non-hazardous atmosphere. The only way of identifying the degradation or loss of gas detection capability is to deliberately apply a known concentration of the target gas to the sensing element and to compare its output to that produced in its original condition. This requires gas detectors employing catalytic, electrochemical or semi-conductor film gas sensing technologies to be routinely tested with target gas in order to maintain a degree of confidence that they will work correctly in the event of a hazardous gas leak.

The requirement for gas detectors to be routinely tested with target gas in order to maintain confidence in their ability to detect gas gives rise to a number of problems and concerns for the users of such detectors. First, the effort and cost associated with the routine gas testing of gas detectors at a typical industrial or petrochemical facility can be very considerable. Second, in order to control operating costs, operators of industrial and petrochemical facilities often only perform testing of their gas detectors at the minimum recommended frequency. This test frequency is not sufficient to meet SIL requirements. Third, problems with individual gas detectors are commonly discovered only when they are tested. Consequently, failure of detectors can often go undiagnosed for months, and this is clearly inadequate for SIL rated systems. Fourth, it is difficult reliably to generate or store toxic gases. And finally, many operators of industrial or petrochemical facilities simply do not want their personnel moving around facilities with pressurized cylinders of toxic or flammable gases.

Infrared gas detectors work by measuring the absorption of infrared radiation at specific wavelengths by the target gas. Compared to catalytic, electrochemical and semi-conductor film gas detectors, infrared gas detectors possess few unrevealed failure modes and are becoming the flammable gas detector of choice for the petrochemical industry. However, despite the relatively small number of unrevealed failure modes in well designed infrared flammable gas detectors, such gas detectors are still subject to gas testing regimes, detectors typically being tested every six or twelve months. Also, whilst users of infrared flammable gas detectors are happy to only gas test their detectors once every six or twelve months, they would appreciate having a means of functionally testing their gas detectors more frequently if this could be done in a quick, cost-effective manner. Furthermore, most currently available infrared gas detectors are only suitable for the detection of flammable gases at concentrations in the range of 1-100% Lower Explosive Limit (LEL). Such infrared gas detectors are not suitable for detecting toxic gases at the low ppm concentrations that are required for most toxic gas detection applications. This leaves users of toxic gas detectors still needing to perform regular gas testing of their toxic gas detectors in order to maintain confidence that they will work correctly in the event of a toxic gas leak.

It is a further object of the present exemplary embodiment to apply LDS technology to provide a hazardous gas detector enabling safety protective systems to meet the safety integrity levels appropriate for most petrochemical facilities by producing a specific distortion pattern of the absorption of radiation by a target gas (which specific distortion pattern characterizes the target gas and for convenience is therefore herein termed a 'fingerprint').

Thus, apparatus according to the exemplary embodiment may include an optical splitter operative to split the radiation into two fractions of which one fraction is transmitted across the monitored space to said first optical receiver and the other is passed through a retained sample of the target gas to a second optical receiver, wherein the control bias current applied to the laser diode is controlled by a feedback signal from said second optical receiver so that absorption of the radiation has a specific distortion pattern for the target gas, characterized in that said distortion pattern includes two harmonics of each of the electrical modulation frequencies, each of substantial magnitude.

The distortion pattern may include an even harmonic and an odd harmonic; and preferably it includes three harmonics to provide two out of three voting and the ability to reconcile unusual measurements.

More particularly considered, this form of the apparatus may comprise a transmitter with a laser diode driven by a current comprising two components, a bias component operating the laser diode at a mean wavelength close to a chosen optical absorption line of the target gas and a sinusoidal wavelength scanning component which cyclically scans the wavelength of the laser diode over the absorption line of the target gas, characterized in that the bias and wavelength scanning components are so controlled that absorption of optical radiation from the laser diode by target gas produces a specific distortion fingerprint including at least two harmonics of the wavelength scanning component frequency each of substantial magnitude and known, fixed magnitude ratio(s) and phase angles, said optical radiation being split into two fractions, one fraction being passed through a retained sample of the target gas and illuminating a first optical detector, the signal from which is used by the transmitter to maintain the conditions necessary for generation of the specific distortion fingerprint, and the second fraction being transmitted through said monitored space to illuminate a second optical detector in a receiver, the signal from said second optical detector being processed in relation to said specific distortion fingerprint to calculate the quantity of target gas present in the monitored space and the receiver providing an output signal representative of the calculated quantity.

BRIEF DESCRIPTION OF THE DRAWINGS

Other features of the invention will be apparent from the following description, which is made by way of example only with reference to the accompanying schematic drawings in which—

DETAILED DESCRIPTION OF EXEMPLARY EMBODIMENTS

Figure 1:
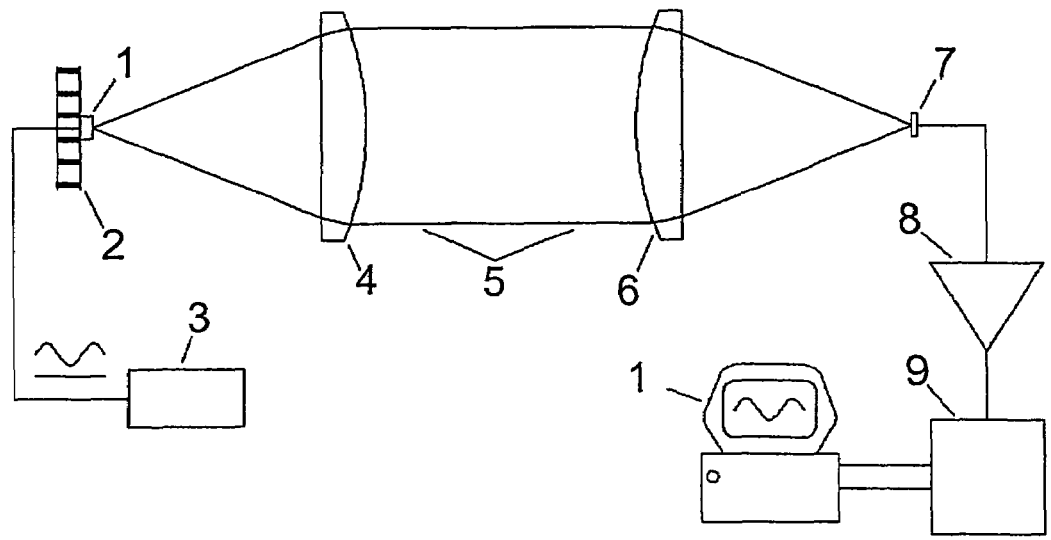
FIG. 1 shows a simple prior art LDS based gas detection or measurement system.

A simple LDS based gas detection or measurement system is shown in FIG. 1 and comprises a laser diode 1, mounted on a temperature stabilized mount 2, driven by a laser diode drive/modulation circuit 3, the output from the laser diode being collected and collimated by an optical element 4. The resulting beam is transmitted through a monitored space 5 to a receiver optical element 5, which focuses the received radiation onto a detector 7. The signal from the detector 7 is amplified by an amplifier 8 and digitized by an analogue to digital converter (ADC) 9, and then processed by a signal processing system 10 to calculate the quantity of target gas in the sample path.

The operation of the system of FIG. 1 is illustrated by FIGS. 2 to 8.

Figure 2:
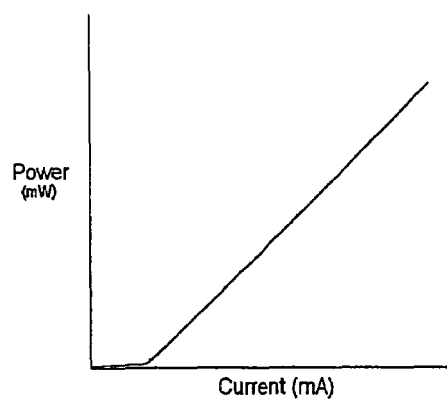
FIG. 2 shows the typical variation in laser diode output power with applied drive current for a laser diode used in a simple prior art LDS based gas detection or measurement system.

FIG. 2 shows the variation in output power from the laser diode as the drive current is increased, this being essentially linear when operating above the laser diode's threshold current.

Figure 3:
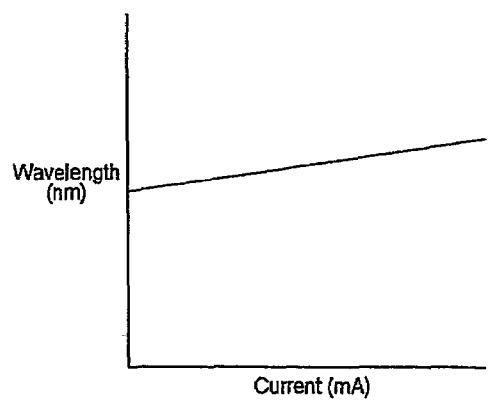
FIG. 3 shows the typical variation in output wavelength with applied drive current for a laser diode used in a simple prior art LDS based gas detection or measurement system.

FIG. 3 shows how the output wavelength of the laser diode varies with drive current, this effect being used to scan the laser's wavelength.

Figure 4:
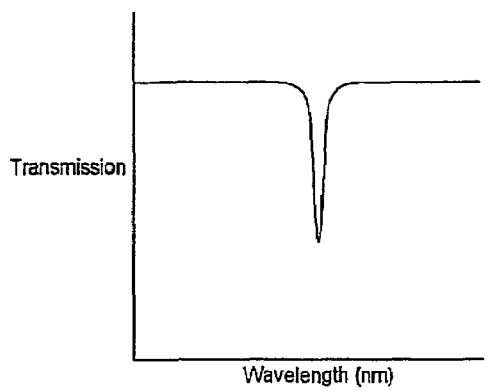
FIG. 4 shows the ideal transmission spectra for a single target gas absorption line to be scanned by a simple prior art LDS based gas detection or measurement system.

FIG. 4 shows the ideal wavelength-dependent transmission in and around the region of a chosen target gas absorption line resulting from introduction of a quantity of target gas into the monitored space. (It should be appreciated that the absorption spectra of gases contain many absorption lines and that FIG. 4 shows a small, ideal region around a particular absorption line chosen for making measurements.)

Figure 5:
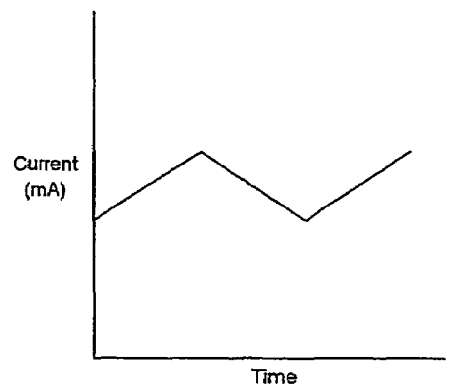
FIG. 5 shows the ramp component of the drive current applied to a laser diode in a simple prior art LDS based gas detection' or measurement system.

The laser diode is driven by a control current comprising two components, a ramped bias component and a sinusoidal modulation component. FIG. 5 shows the bias component, which is used to slowly scan the mean wavelength of the laser diode over the region containing the chosen target gas absorption line.

Figure 6:
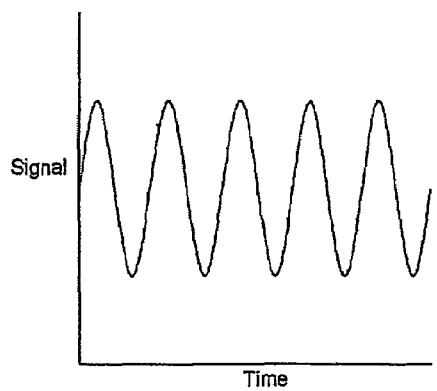
FIG. 6 shows the sinusoidal component of the drive current applied to a laser diode in a simple prior art LDS based gas detection or measurement system.

FIG. 6 shows the sinusoidal component, which is used to quickly scan the wavelength over a small wavelength region, typically around 0.05-0.1 nm. In the absence of target gas in the monitored space, the signal from the system's detector effectively replicates the combined current waveform applied to the laser diode.

Figure 7:
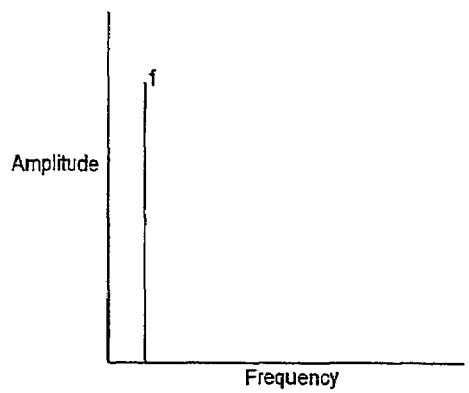
FIG. 7 shows the Fourier transform of the detector signal for a simple prior art LDS based gas detection or measurement system when there is no target gas in the monitored space.

FIG. 7 shows the output from the system's detector during a single sinusoidal wavelength scan when a substantial quantity of target gas is present in the Monitored space. Those skilled in the science will note the deviation from a simple sinusoidal waveform produced by absorption of optical radiation when the wavelength of the laser diode scans across the target gas' absorption line. This waveform distortion generates components at harmonics of the sinusoidal wavelength scanning frequency, with second and third harmonics predominating. By processing the detector signal it is possible to measure the size of the second or third harmonic components as the mean wavelength of the laser diode is ramped over the region containing the absorption line.

Figure 8:
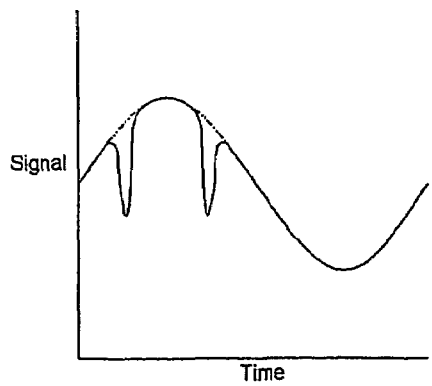
FIG. 8 shows the signal from the optical detector when there is a substantial quantity of target gas present in the monitored space of a simple prior art LDS based gas detection or measurement system.
Figure 9:
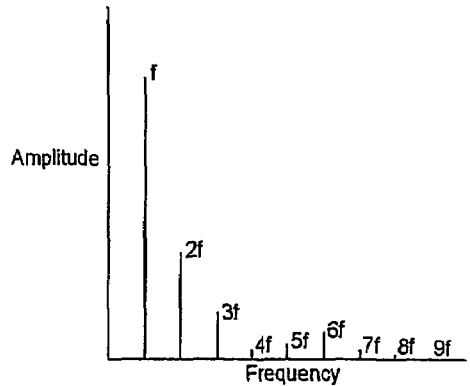
FIG. 9 shows the Fourier transform of the detector signal when there is a substantial quantity of target gas present in the monitored space of a simple prior art LDS based gas detection or measurement system.

FIG. 8 shows the variation in second harmonic as the laser diode's wavelength is ramped over the region containing an absorption line. There are three regions on this curve of particular interest, marked a, b and c. Regions a and c correspond to parts of the ramp cycle where there is no overlap of the laser diode wavelength with the target gas absorption line. These regions can be used to estimate the size of the second harmonic component in the absence of target gas absorption. Region b corresponds to the part of the ramp cycle with the greatest overlap between the laser diode wavelength and the target gas absorption line. The size of the change in the second harmonic component in this region relative to regions a and c is proportional to the amount of target gas present in the monitored space. Typically LDS is used to measure the change in the second or third harmonic components as the laser diode's wavelength is ramped over the region of the target gas absorption line in order to determine the amount of target gas present in the monitored space.

Various methods can be used to measure the size of the harmonic components, the most popular of which is synchronous detection/demodulation. Alternatively, the signal can be digitized as is shown in FIG. 1 and then processed using digital signal processing techniques to measure the magnitude of the various frequency components in the detector signal.

LDS techniques similar to those illustrated in FIGS. 1 to 8 have been widely used in instrumentation to measure gases in industrial processes and to monitor atmospheric pollutants, where fractional absorbances of the order of $1\times10^{-4}$ to $1\times10^{-5}$ are detected or measured with reliability acceptable for such applications. However, equipment using LDS techniques has rarely been used for detecting toxic or flammable gases for safety purposes. (One exception is the use of LDS equipment in detecting hydrogen fluoride at aluminium smelters and hydrocarbon alkylation plants. This has been possible because hydrogen fluoride has a very large absorption cross-section in the 1310 nm region, making it possible to detect ppm concentrations of HF by detecting fractional absorbances of the order of $1\times10^{-2}$ to $1\times10^{-3}$, which is relatively straightforward).

Hazardous gases that could usefully be detected by LDS based detectors if the false alarm problem could be overcome include hydrogen sulphide, ammonia, hydrogen chloride, hydrogen cyanide, methane and vinyl-chloride monomer.

The main reason that LDS has not been widely employed for the detection of toxic or flammable gases for safety related applications is that such applications demand an extremely high level of reliability and, in particular, very low false alarm rates, which cannot be achieved by conventional LDS equipment. With the consequences of false alarms from gas detectors including the shutting down of large industrial or petrochemical plants, personnel donning safety equipment and commencing evacuation procedures; and a loss of confidence in a gas detection system, users of fixed gas detection equipment are looking for false alarm rates for each gas detector of less than 1 per 100 years. Whilst existing LDS based equipment might be able to detect or measure fractional absorbances of the order of $1\times10^{-4}$ to $1\times10^{-5}$ with reliability acceptable for process control or atmospheric monitoring applications, such small fractional absorbances cannot be detected with an acceptably low false alarm rate for safety applications.

High Sensitivity Gas Detection

Three main problems are met in attempting to detect fractional absorbances of $1\times10^{-4}$ to $1\times10^{-5}$ using an LDS system similar to that shown in FIG. 1 reliably and with a false alarm rate that is low enough for use in safety related applications. The three problems are system noise, absorption(s) by atmospheric gases and coherence/fringe effects, and these problems will now be discussed.

System noise is introduced by virtually all of the active components used in the LDS system of FIG. 1, including the laser diode drive circuit 3, the laser diode 1, the detector 7, the amplifier 8 and the ADC 9. These differing noise sources exhibit complex frequency and probability distributions, making it practically impossible to determine their influence upon false alarm rates in a regime where effects with probabilities as low as once in a thousand years are potentially significant. All that can be stated with confidence is that for an LDS system to experience a system noise induced signal deviation of less than $1\times10^{-5}$ for a period long enough to cause a false alarm just once in one hundred years of operation would require an exceptionally high system signal to noise ratio ($>1\times10^6:1$). In practice, even with careful design and selection of components, sub-systems and signal processing routines, achieving such a high system signal to noise ratio is not possible. Furthermore, even if it were possible to achieve such a high system signal to noise ratio in ideal conditions, the signal losses associated with the operation of an LDS system outdoors over a useful path-length preclude achieving such a signal to noise ratio in operational service. Therefore, any LDS system looking to detect fractional absorbances of $1\times10^{-5}$ with an acceptably low probability of false alarms for use in safety related applications must address the problem of the signal to noise ratio requirement associated with LDS systems similar to that of FIG. 1.

When making optical measurements along an open path through the atmosphere it is essential to consider the effects of absorption by the gases that constitute the atmosphere. In particular, atmospheric gases such as oxygen, carbon dioxide and water vapour exhibit strong optical absorption at wavelengths from the near infrared to the far infrared, which is the wavelength region of main interest for LDS systems. When assessing wavelengths at which to make measurements of a particular target gas it is necessary to ensure that there are no strong atmospheric absorption lines at wavelengths very close to that of the absorption line(s) of the target gas, and also that any continuum absorption by the atmospheric gases will not attenuate radiation at the candidate wavelength to such an extent that the system's signal to noise ratio will be unduly compromised. Additionally, when looking to detect fractional absorbances as low as $1\times10^{-5}$, it is necessary to consider the effects that might be introduced when attempting to make measurements in the far wings of strong atmospheric absorption lines, because even if the line is relatively distant and the atmospheric transmission is acceptably high, the curvature of the transmission in the far wings of a strong absorption line can look similar to the curvature produced by a small absorption produced by the target gas.

For atmospheric gases such as oxygen and nitrogen which have relatively stable atmospheric concentrations, it is possible to compensate for any small reading offsets that their absorptions might introduce. This can be done either by zeroing the instrument or detector when it is installed, or by applying a correction calculated for the length of the monitored space from the characterized effects of the atmosphere upon the instrument or detector. However, for atmospheric gases such as water vapor, carbon dioxide and carbon monoxide which exhibit significant variation in concentration depending upon weather, geography and any local emissions of these gases, such compensation is not possible. Therefore, when designing an LDS system to make high sensitivity measurements along an open atmospheric path it is necessary to pay particular attention to the effects of absorption by water vapor, carbon dioxide and carbon monoxide. Any technique that can reduce the potential for such absorptions to interfere with equipment using LDS is highly beneficial.

The diode lasers used in LDS systems exhibit a high degree of spatial and temporal coherence, which means that light reflected or scattered from virtually anywhere within the LDS system or monitored space can interact in a coherent manner with the light proceeding directly along the intended measurement path. The consequence of such coherent interactions is unwanted amplitude modulation of the light proceeding along the measurement path, such modulation being particularly undesirable if it produces features similar to those produced when the laser's wavelength is scanned across an absorption line of the target gas. This problem is exacerbated by the fact that the amplitude of any such modulation is dependent upon the field strength of a particular reflection or scattering source, not upon the intensity of such a source. This means that amplitude modulations of $1 \times 10^{-5}$ can be produced by reflected or scattered light of $1 \times 10^{-10}$ intensity relative to that of the beam with which they are interacting. In effect, reflected or scattered light is capable of modulating the intensity of the light proceeding along the intended measurement path by far more than its own intensity.

With relative intensities of $1 \times 10^{-10}$ capable of producing amplitude modulations of $1 \times 10^{-5}$, coherence/fringe effects are a very significant problem in LDS systems. Indeed, much work upon the enhancement of systems using LDS has revolved around developing techniques to reduce the magnitude or overall impact of coherence/fringe effects upon such systems. This work has included the development of a number of prior techniques to combat coherence/fringe effects, such as those described in U.S. Pat. No. 4,684,258 and U.S. Pat. No. 4,394,816.

Despite the introduction of techniques to reduce the significance of coherence/fringe effects upon LDS systems, in many instances, coherence/fringe effects still set the limit of detection or measurement for such systems. Also, whilst these techniques are adequate in relatively benign, controlled environments, they work less well in outdoor or uncontrolled environments and are not sufficient to deal with the challenges presented by extreme environments. Consequently, if an LDS system is to be used to detect fractional absorbances of $1 \times 10^{-5}$ in industrial safety applications its design must address the coherence/fringe problem in a manner that works with the highest reliability even when exposed to extreme environmental conditions.

For an LDS system as described in FIGS. 1 to 8, modulating the laser at a frequency f and measuring at harmonic frequency $f_1$, the probability of system noise $N(f_1)$ producing a false alarm size deviation $\Delta(f_1)$ in a given measurement interval T, can be described by an equation of the form below, where $k_1$ is a constant for the system relating noise to probability of deviation $P(\Delta(f_1(T)))$—

$$P(\Delta(f_1(T))) = k_1 . N(f_1) . T^{-1/2}$$

Figure 10:
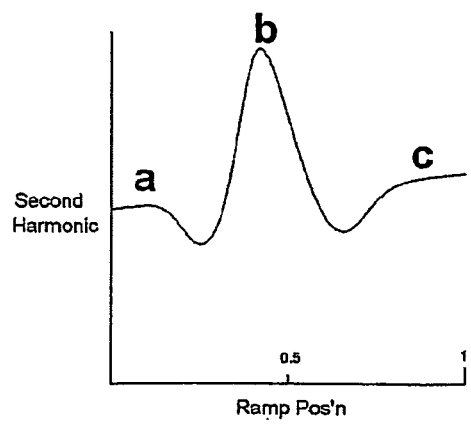
FIG. 10 shows the variation in second harmonic as the laser diode's wavelength is ramped over the region containing an absorption line.
Figure 13:
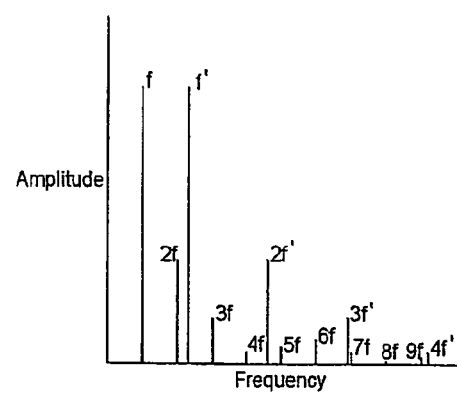
FIG. 13 shows the combined Fourier transform of the detector signal when there is a substantial quantity of target gas present in the monitored space of a system with a laser driven as shown in FIG. 11.

According to the present invention, the laser diode is driven by a current as shown in FIG. 10, comprising two components, a bias component and a sinusoidal component, the bias component alternating between two current levels A and B, chosen to operate the laser diode at two mean wavelengths $\Lambda_1$ and $\Lambda_2$, close to two separate optical absorption lines of the same target gas, the sinusoidal component synchronously alternating between two, non-harmonically related electrical frequencies f and f' at which the laser's wavelength is scanned across one or the other of the chosen absorption lines for an interval T/2. When there is no gas present in the measurement path, the combined Fourier transform of the detector signal for a total interval T (where $T \gg 1/f_1$) will look like FIG. 13, with just two frequency components f and f'. When there is a substantial quantity of target gas in the monitored space, the combined Fourier transform of the detector signal will look like FIG. 11, with sets of harmonics of both f and f'. When measured at frequencies $f_1$ and $f_2$ for intervals of T/2, the probability of system noise producing a false alarm size deviation ($\Delta(f)$) during each separate T/2 interval is as follows —

$$P(\Delta(f_1(T/2))) = k_1 . N(f_1) . T^{-1/2} . \sqrt{2}$$

$$P(\Delta(f_2(T/2))) = k_2 . N(f_2) . T^{1/2} . \sqrt{2}$$

If measurement frequencies $f_1$ and $f_2$ are chosen to be the same order harmonics of f and f' and the system noise at $f_1$ and $f_2$ is the same, the probability that during a combined measurement interval (T/2+T/2) the quantities of target gas $Q_1$ and $Q_2$ calculated to be present in the measurement path will exceed a false alarm size deviation ($\Delta(f)$) due to system noise is—

$$P(\Delta(f_1(T/2))) \& P(\Delta(f_2(T/2))) = k_1 . N(f_1) . T^{-1/2} \sqrt{2} \times k_2 . N(f_2) . T^{-1/2} . \sqrt{2}$$

For $N(f_1) = N(f_2)$ this simplifies to—

$$P(\Delta(f_1(T/2))) \& P(\Delta(f_2(T/2))) = 2.k_1.k_2.N(f_1)^2.T^{-1}$$

Since in most instances $P(\Delta(f_1(T/2)))$ and $P(\Delta(f_2(T/2)))$ are small, the probability of both measurements suffering noise induced deviations sufficient to exceed an alarm threshold during interval T is very small. By way of example, a system with a noise floor sufficient to achieve an average false alarm rate of 1 in 2 days when modulating at a single frequency around a single absorption line could be improved to achieve an average false alarm rate as low as 1 in 100 years by measuring at an additional frequency and wavelength where the average false alarm rate was 1 in 10 hours and using the second measurement to confirm the first.

In order to achieve the best results, the use of quantities $Q_1$ and $Q_2$ for calculation of the amount of gas in the monitored space should be in combination with results for previous measurements, using rules dependent upon the quality of agreement between the quantities. These rules and their intended effects are as follows —

RA1 If $Q_1$ and $Q_2$ are in close agreement, a large fraction of the average of $Q_1$ and $Q_2$ is added to a balancing fraction of the running average of previous results for calculating the quantity of gas present in the monitored space. This enables the output from the apparatus to quickly track changes in the quantity of target gas present in the monitored space when confidence in the most recent measurements is high.

RA2 If $Q_1$ and $Q_2$ are in reasonable but not close agreement, a lesser fraction of the average of $Q_1$ and $Q_2$ is added to a larger balancing fraction of the running average of previous results for calculating the quantity of gas present in the monitored space. This enables the output to take account of the most recent measurements whilst reducing the impact that potential errors in these measurements might have upon the output of the apparatus.

RA3 If only $Q_1$ or only $Q_2$ is in close or reasonable agreement with the running average of previous measurements, the quantity which is not in close or reasonable agreement is rejected whilst a small fraction of the close or reasonably agreeing quantity is added to a larger balancing fraction of the running average of previous results for calculating the quantity of gas present in the monitored space. This enables measurements in which confidence is low to be prevented from affecting the output from the apparatus; whilst allowing measurements in which there is confidence to contribute to keeping the output from the apparatus up to date.

RA4 If $Q_1$ and $Q_2$ are in poor agreement with each other and the running average of previous measurements, both $Q_1$ and $Q_2$ are rejected and the calculation of the quantity of gas present in the monitored space is based solely upon the running average of previous results, the balancing fraction being set to unity. This enables false alarms due to measurements in which confidence is low to be effectively eliminated whilst maintaining the output from the apparatus at the most recent level in which confidence is acceptably high.

Modulation and measurement at a number of non-harmonically related frequencies does not only confer benefits in terms of lessening the impact of classic, thermal noise. Electronic systems are often required to operate in environments affected by electromagnetic interference. Unlike classic, thermal noise, electromagnetic interference tends to be at frequencies that are harmonically related to the frequencies of operation of the equipment that are the source of the interference. Therefore, the use of modulation at a number of non-harmonically related frequencies reduces the likelihood that electromagnetic interference will affect all measurement frequencies simultaneously, enabling false alarms due to electromagnetic interference to be reduced.

The present invention also addresses the problems associated with absorption(s) by atmospheric gases when measuring along open paths, as will now be illustrated by considering the effects of absorption by atmospheric gases when attempting to detect or measure hydrogen sulphide.

Figure 14:
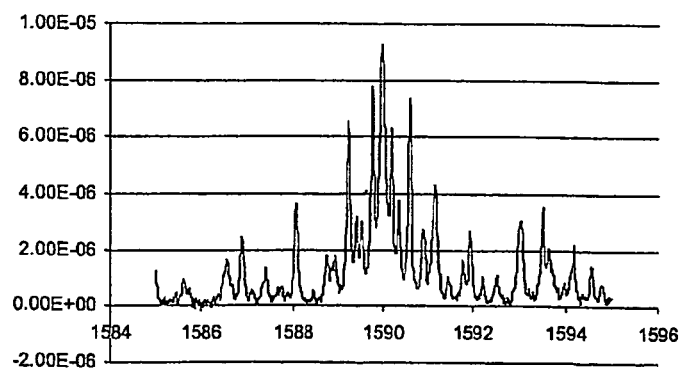
FIG. 14 shows the absorption spectrum for 25 ppm.m of hydrogen sulphide between 1585 nm and 1595 nm.
Figure 15:
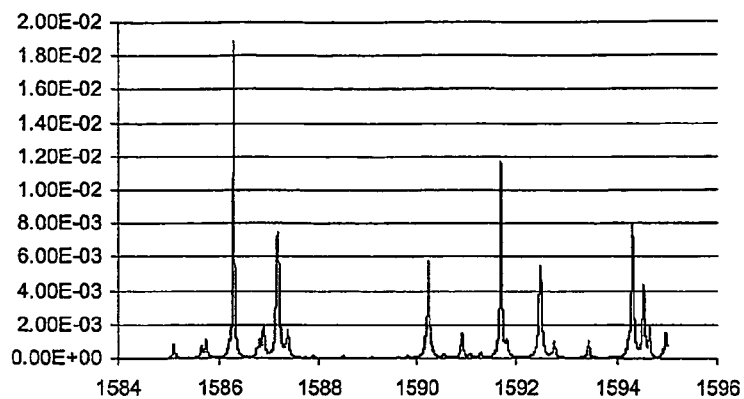
FIG. 15 shows the absorption spectrum for a 100 metre path through the Earth's atmosphere at 30° C., 100% RH between 1585 nm and 1595 nm.
Figure 16:
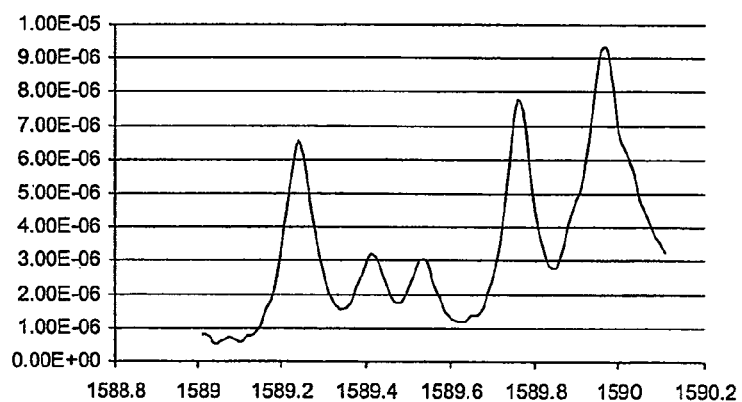
FIG. 16 shows the absorption spectrum for 25 ppm.m of hydrogen sulphide between 1589 nm and 1590.1 nm.
Figure 17:
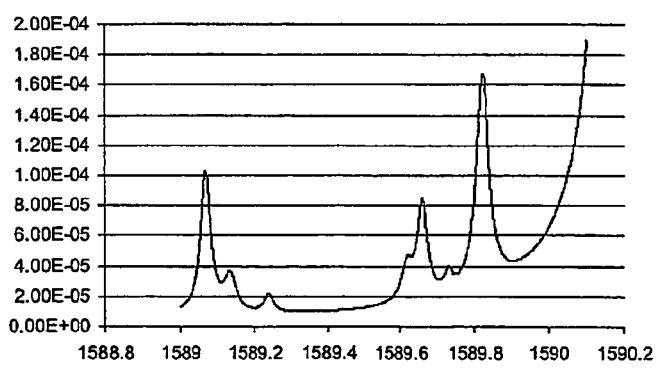
FIG. 17 shows the absorption spectrum for a 100 metre path through the Earth's atmosphere at 30° C., 100% RH between 1589 nm and 1590.1 nm.

Hydrogen sulphide is a highly toxic gas with a Threshold Limit Value (TLV) of 10 ppm and relatively weak optical absorption in the wavelength regions accessible to the LDS technique. For an LDS based hydrogen sulphide detector to be of use for safety applications it needs to be capable of detecting a 5 metre diameter cloud of gas containing hydrogen sulphide at 50% TLV (5 ppm). This corresponds to 25 ppm.m of hydrogen sulphide, which will produce a maximum fractional absorbance of the order of $1\times10^{-5}$ in the 1560 nm to 1620 nm region where the best absorption lines for hydrogen sulphide detection using LDS are found. FIG. 14 shows the absorption spectrum of hydrogen sulphide between 1585 nm and 1595 nm for 25 ppm.m of hydrogen sulphide and FIG. 15 shows the corresponding absorption spectrum for a 100 metre path through the atmosphere at sea-level, 100% RH, 30° C. The 1585 nm to 1595 nm wavelength region is particularly good for the detection of hydrogen sulphide, suffering from lower levels of atmospheric absorption than found elsewhere between 1560 nm and 1620 nm. However, despite this there are still some relatively strong absorption features present due to carbon dioxide, water vapour and carbon monoxide. The conventional approach used in LDS systems to reduce the effect of such absorptions would be to choose the target gas absorption line at which to make measurements very carefully, to minimise the effects of such lines. In this example, choosing a hydrogen sulphide absorption line in the 1589 nm to 1590.1 nm region looks a very good option (see FIGS. 14 and 15), but even in this exceptionally clear region, close inspection reveals a number of significant features arising from atmospheric gases, including complete absorption lines and baseline curvature due to distant, strong lines. The only region where atmospheric absorption is less than $1\times10^{-5}$ is 1589.3 nm to 1589.45 nm but this is a region where the strongest hydrogen sulphide line will only produce a fractional absorbance of $3\times10^{-6}$ for 25 ppm.m of hydrogen sulphide. The hydrogen sulphide line at 1589.97 nm produces a fractional absorbance of almost $9.3\times10^{-6}$ for 25 ppm.m but the atmospheric absorption due to a strong water vapour line nearby is $5.5\times10^{-5}$ and is increasing very rapidly with wavelength. Consequently, there is a significant likelihood of atmospheric water vapour influencing any measurements made at 1589.97 nm.

Figure 11:
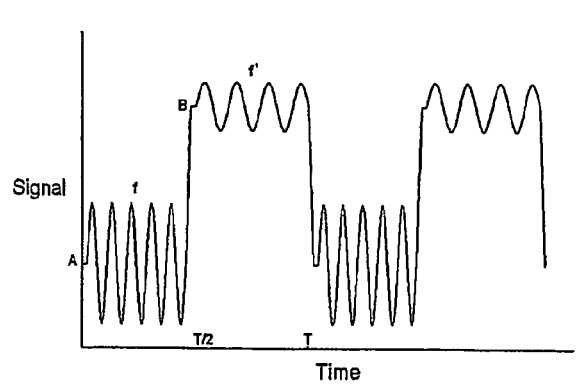
FIG. 11 shows a laser diode drive current waveform comprising two alternating bias and frequency components.
Figure 12:
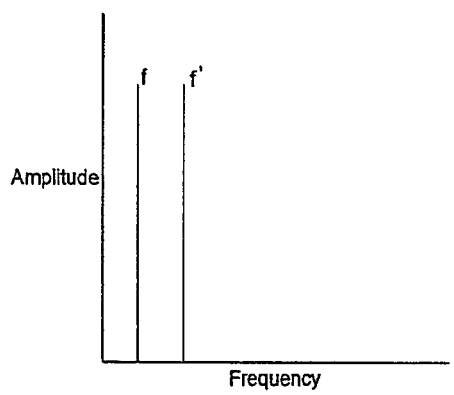
FIG. 12 shows the combined Fourier transform of the detector signal when there is no target gas present in the monitored space of a system with a laser driven as shown in FIG. 11.

If the laser diode drive current is modulated with a waveform similar to that shown in FIG. 11, such that it alternately scans the region around the hydrogen sulphide absorption line at 1589.42 nm at frequency f for a period T/2 and the region around the hydrogen sulphide line at 1589.97 nm at frequency f' for a period T/2, two calculations of the quantity of hydrogen sulphide present in the path can be made at frequencies $f_1$ and $f_2$ and compared. If this comparison is performed in such a manner that a hydrogen sulphide alarm reading is only signalled when both measurements agree within a reasonable tolerance about the presence and amount of hydrogen sulphide gas in the monitored path, false alarms due to atmospheric absorption and/or insufficient system signal to noise ratio can be greatly reduced. A calculated quantity $Q_1$ based upon slightly noisy measurements at 1589.42 nm needs to be confirmed by a similar calculated quantity $Q_2$ for the less noisy measurement at 1589.97 nm; whilst a calculated quantity $Q_2$ for measurements potentially influenced by atmospheric water vapour absorption at 1589.97 nm needs to be confirmed by a similar calculated quantity $Q_1$ at 1589.42 nm where the effects of absorption by atmospheric water vapour are negligible.

Also, since measurements at 1589.42 nm are not affected by water vapour, they can be used to keep track of any effects of water vapour absorption on the measurements made at 1589.97 nm, allowing such effects to be compensated for. When used in this manner, the lower signal to noise ratio of measurements at 1589.42 nm is not a significant problem, since the effects of water vapour will not normally change quickly and any compensation can be based upon the average of measurements made over a number of minutes.

Thus measurements made at 1589.42 nm provide three benefits. First, they enable a reduction in the probability of false alarms due to system noise when compared and combined with the results of measurements made at 1589.97 nm. Second, they enable the effects of water vapour absorption upon measurements at 1589.97 nm to be reliably discriminated from the effects of any changes in the amount target gas concentration in the monitored space. Using this information it is possible to subtract the effects of water vapour absorption from measurements at 1589.97 nm without compromising the ability of the apparatus to detect hydrogen sulphide. And third, they eliminate the possibility that even very sudden changes in atmospheric water vapour concentration can result in false alarms or spurious readings. Even if there has not been sufficient time to use the measurements at 1589.42 nm to accurately compensate for the effects of water vapour absorption at 1589.97 nm, the 1589.42 nm measurements will not confirm the presence of hydrogen sulphide in its absence.

These three benefits cannot be achieved by simply modulating at a single frequency with amplitude sufficient to scan the wavelength range encompassing the two absorption lines to be measured, for a variety of reasons. First, there are a number of very strong atmospheric absorption lines between 1589.42 nm and 1589.97 nm and if the laser is scanned over these lines whilst measurements are being taken, these lines will introduce harmonic frequency components which will seriously interfere with measurements of the weaker hydrogen sulphide absorption lines. Next, scanning and measuring in this manner does not allow the magnitude of absorption at 1589.42 nm and 1589.97 nm to be measured independently, preventing use of results at 1589.42 nm for compensation of the effects of water vapour upon measurements at 1589.97 nm. And finally, scanning and measuring at a single frequency does not provide the false alarm rate improvement that can be achieved by scanning, measuring and comparing results for two, non-harmonically related frequencies.

The technique of modulating the laser such that it sweeps two distinct wavelength regions around two separate absorption lines of a single target gas at two differing modulation frequencies f and f', followed by comparison of the two measurement results to confirm that they are within an acceptable agreement tolerance can be beneficially employed in a number of different scenarios including those where— a) The target gas has a relatively weak absorption line in a region of low atmospheric absorption and a stronger absorption line in a region of higher atmospheric absorption;

b) The target gas has two weak absorption lines in a region of low to moderate atmospheric absorption; and/or c) The target gas has two strong absorption lines in regions affected by absorption by different atmospheric gas species.

For hydrogen sulphide, there are absorption lines at 1582.13 nm, 1589.24 nm, 1589.42 nm, 1589.54 nm, 1589.97 nm and 1593.05 nm which might usefully be combined in the ways described to produce a highly reliable hydrogen sulphide detector.

The present invention also addresses the problems associated with coherence/fringe effects, which effects often set the minimum measurement or detection limit in LDS based instrumentation or detection equipment.

The amplitude modulation produced by coherent interference exhibits a sinusoidal variation with wavelength. For coherent light of wavelength $\Lambda$, the phase difference, expressed as a number of wave cycles $\phi_n$, between light leaving an optical surface and light returning having been reflected at a distance D from this optical surface is given by —

$$\phi_n = 2D/\Lambda$$

The amplitude modulation produced by coherent interference between light leaving an optical surface and light returning from reflection at a distance D from an optical surface will go through a single sinusoidal cycle for a change in wavelength $\partial \Lambda$, given by equation —

$$(\Lambda + \partial \Lambda) = 2D/(\phi_n - 1)$$

Figure 18:
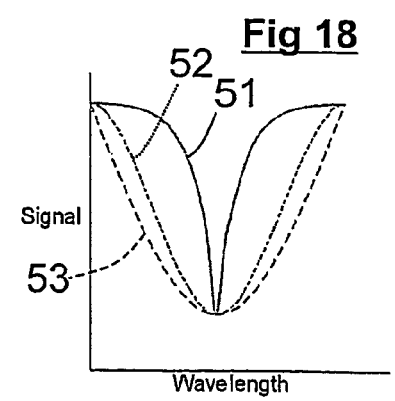
FIG. 18 shows the shape of a gas absorption line compared to a half and full cycle of a sinusoid, typical of that produced by coherence/fringe effects.

FIG. 18 shows the amplitude modulation produced when the wavelength of a laser diode is scanned over a target gas absorption line 51, a half cycle of a sinusoid 52 and a full cycle of a sinusoid 53, all fitted to the same wavelength interval. FIG. 18 shows that if the period of the sinusoidal modulation produced by coherence/fringe effects is of approximately the same width as the target gas absorption line, there is a probability that such modulation will start to correlate and interfere with the measurement or detection of the target gas absorption line.

Even with extremely careful design and engineering of an LDS system it is not possible to completely eliminate coherence/fringe effects from such systems: it is only possible to reduce their size or impact upon system performance. For LDS systems making measurements through open atmospheric paths, the situation is made considerably more difficult by the lack of control over what happens in the open part of the system. For instance, light can be scattered or reflected in the open path by rain-drops, snow, fog, mist, people or vehicles moving through the path. This results in light being scattered or reflected at distances and intensities over which can be controlled little if at all. For an LDS system intended to make measurements along an open path therefore, there is always the possibility of light being reflected or scattered at a distance that will create coherent fringes with a period which will correlate and interfere with the measurement of a target gas absorption line.

Figure 19:
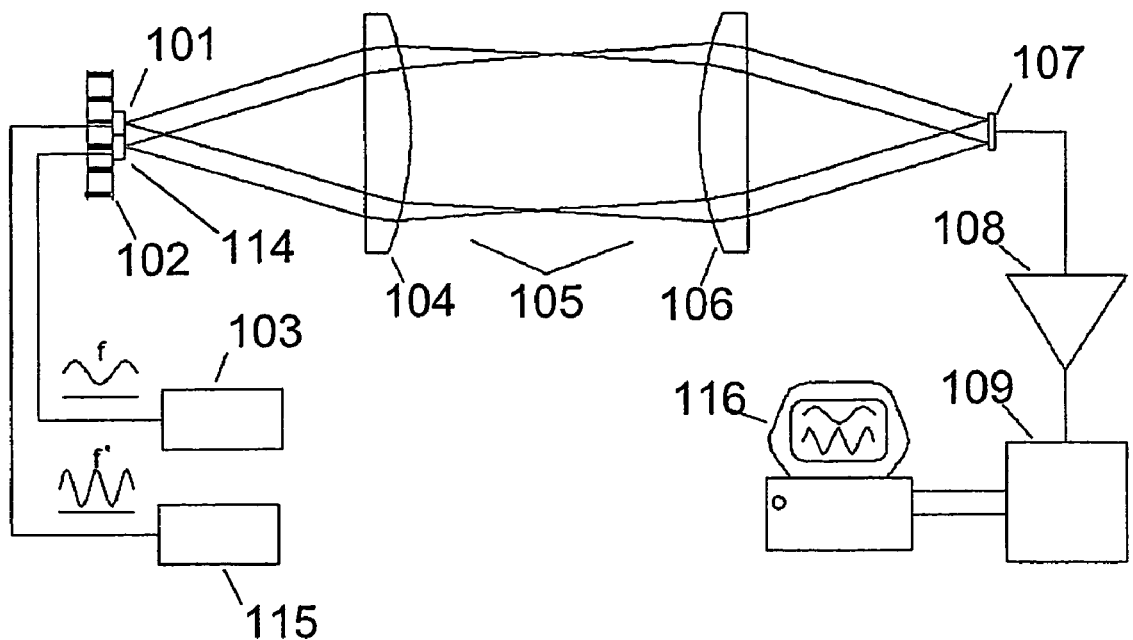
FIG. 19 shows a dual laser, dual frequency, dual wavelength laser diode gas detection or measurement apparatus embodying the present invention.

While it is not possible to eliminate coherence/fringe effects from an LDS system, especially one operating along an open measurement path, it is possible to reduce the rate of false alarms arising from such effects by using apparatus as shown in FIG. 19, comprising an embodiment of the present invention. The apparatus shown in FIG. 19 contains two laser diodes 101 and 114, operating at mean wavelengths $\Lambda_1$ and $\Lambda_2$, these wavelengths corresponding to two different absorption lines of the same target gas. Lasers 101 and 114 are on a common temperature stabilized mount 102 and are driven by drive circuits 103 and 115 at electrical frequencies f and f' and scanned over wavelength ranges $\delta \Lambda_1$ and $\delta \Lambda_2$ respectively. The outputs from lasers 101 and 114 are collimated by a common optical element 104, aligned such that optical radiation from both lasers reaches receiver optical element 106 after passing through monitored space 105. Receiver optical element 106 focuses optical radiation from both lasers onto a receiver detector 107, at which point the optical signals are effectively combined into a single electrical signal with principal frequency components f and f'. The signal from detector 107 is amplified by amplifier 108, digitized by ADC 109 and processed by a signal processing system 116.

The electrical signal from detector 107 contains two sets of independent frequency components proportional to the amount of target gas present in the measurement path. A quantity of target gas $Q_1$ is calculated from the amplitude of frequency component $f_1$ for measurements made around wavelength $\Lambda_1$ whilst scanning over a range $\partial \Lambda_1$; and a quantity of target gas $Q_2$ is calculated from the amplitude of frequency component $f_2$ for measurements made around wavelength $\Lambda_2$ whilst scanning over a range $\partial \Lambda_2$. These effectively independent measurements of the quantity of target gas in the monitored space can then be compared and treated as described earlier.

When addressing the problems associated with coherence/fringe effects, the use of two laser diodes in a configuration as illustrated by FIG. 19 has three benefits as follows a) Wavelengths $\Lambda_1$ and $\Lambda_2$ can be chosen independently, enabling a larger difference between these wavelengths to be realized than is possible when using a single laser to scan two absorption lines of the same target gas. This larger wavelength difference will result in significantly different coherence/fringe modulation periods when light from the two lasers is scattered or reflected by a common surface at a distance large compared to the wavelength ($\gg 1000 \times \Lambda$). Consequently, the probability of coherence/fringe effects due to scattering or reflection simultaneously producing the same net interference effect at both measurement wavelengths is greatly reduced.

b) The lasers can be scanned over significantly different wavelength ranges, making it possible to ensure that light scattered or reflected from a single surface at a distance D cannot produce a sinusoidal amplitude modulation with a period closely correlated to that of the target gas absorption line for both of the lasers. In effect, there are two characteristic distances D and D' corresponding to $\partial\Lambda_1$ and $\partial\Lambda_2$ respectively, at which scattering or reflection could be a problem for one laser but not the other. By deliberately spacing these characteristic distances such that they never coincide and are not harmonically related, scattering or reflection from a single surface cannot significantly interfere with both measurements at the same time.

c) The physical separation in x, y and z between the two lasers reduces the probability that light scattered or reflected from a common surface will introduce modulation with the same amplitude and phase onto both laser outputs. If necessary, the lasers can be deliberately mounted in positions at which common-mode interference will be further reduced.

In addition to the above benefits with relation to coherence/fringe effects, the use of two lasers operating at mean wavelengths $\Lambda_1$ and $\Lambda_2$, scanning ranges $\partial\Lambda_1$ and $\partial\Lambda_2$ at frequencies f and f', with measurement of frequency components $f_1$ and $f_2$ has other benefits as follows— d) Both of the lasers can be operated at their mean wavelengths whilst also producing optimum output power, enabling each measurement of target gas absorption to be performed upon signals of optimal amplitude and consequently optimal signal to noise ratio.

e) The choice of measurement wavelengths is not limited to the scanning range of a single laser. Wavelengths can be chosen with considerable freedom, enabling for instance two strong, distant lines to be measured, or two lines with low atmospheric interference to be measured, or two lines which are subject to interference by different atmospheric gases to be measured.

f) Since each laser is scanning their target gas absorption line at one frequency, one hundred percent of the time, there is no system signal to noise reduction such as that associated with scanning a single laser alternately at two frequencies.

g) The use of two lasers, scanning different wavelengths at different electrical frequencies makes it possible to treat each measurement as being completely independent of the other. Statistical calculations of the improvement in false alarm rate achieved can be relied upon when used to calculate false alarm probabilities that are too low to be measured by any economically justifiable programme of tests.

Figure 20:
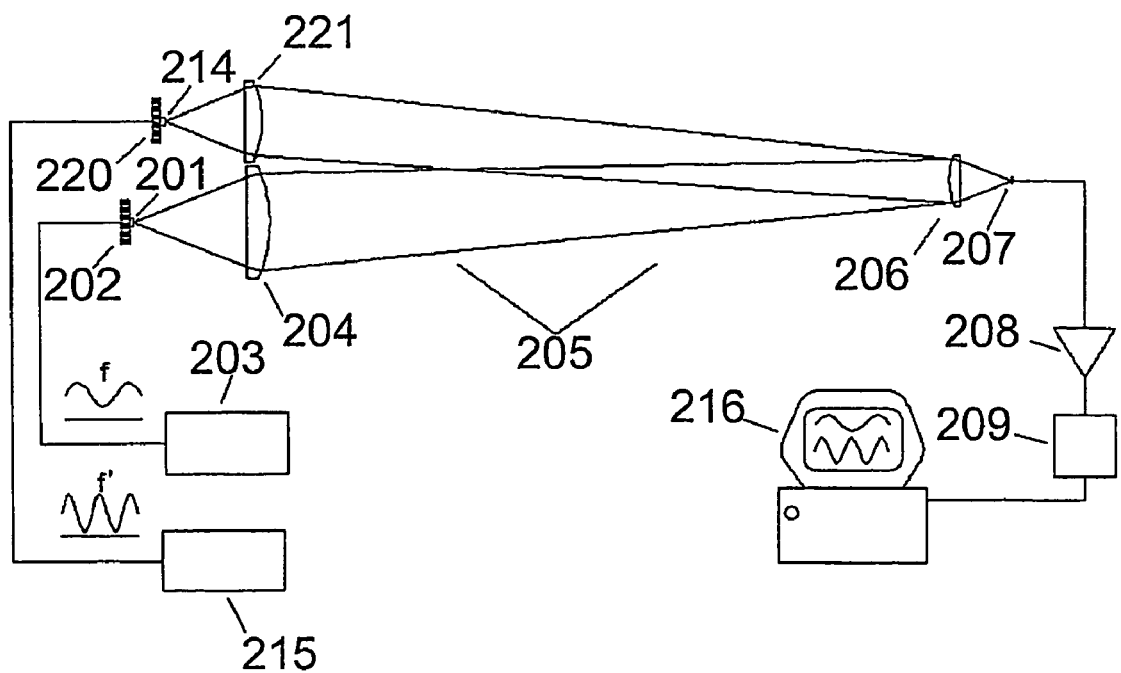
FIG. 20 shows a dual laser, dual frequency, dual wavelength laser diode gas detection or measurement apparatus with dual transmitter optics comprising another embodiment of the present invention.

Another embodiment of the present invention, which reduces the probability of false alarms or spurious readings due to coherence/fringe effects, is illustrated in FIG. 20. In the apparatus of FIG. 20, laser diodes 201 and 214 are respectively mounted on separate temperature stabilized mounts 202 and 220 and their radiation is separately collected and collimated by respective transmitter optical elements 204 and 221 prior to transmission through a monitored space 205 to a receiver optical element 206 which focuses the radiation from both transmitter lasers onto an optical detector 207. The lasers 201 and 214 are driven by respective drive circuits 203 and 215 at electrical frequencies f and f' and scanned over wavelength ranges $\partial\Lambda_1$ and $\partial\Lambda_2$ respectively. The signal from the detector 207 is amplified by an amplifier 208, digitized by ADC 209 and processed by a signal processing system 216. The optical elements 204, 206 and 221 are all chosen to have effective focal lengths and thicknesses which are different from each other by non-harmonic factors.

When addressing the problems associated with coherence/fringe effects, the use of apparatus as shown in FIG. 20 has two benefits as follows— a) The separate optical paths within the transmitter for laser diodes 1 and 14 can be designed to ensure that there are no interference fringes with common periods affecting the outputs of both lasers. In particular, by using optical elements with different focal lengths and different thicknesses, it is possible to ensure that the unavoidable fringes resulting from reflection or scattering of light from the surfaces of these elements will have substantially different, non-harmonically related periods.

b) The use of separate optical elements with different focal lengths for each laser diode means that in the event of the build up of snow, condensation or contamination upon any exposed surfaces of the transmitter's optical elements, the optical radiation scattered or reflected back to each laser diode will be different in intensity and distribution. This is important because the interaction between a laser diode and back-scattered or back-reflected radiation is unstable and chaotic. The chaotic nature of this interaction introduces the possibility that oscillations or disturbances can appear on the output of the laser diode with periods that could not occur due to simple coherent interference. With two lasers experiencing different intensities and distributions of back-scattered or back-reflected radiation, the probability that both will simultaneously produce outputs which contain components which look like those of the target gas is greatly reduced.

The use of separate optical paths with optical elements of different effective focal lengths and thicknesses in the transmitter as illustrated in FIG. 20 can be extended to include separate optical paths with optical elements of different effective focal lengths and thicknesses in the receiver. Applying this approach to the receiver enables apparatus with other configurations to be realized, and conferring similar benefits to those afforded apparatus configured as illustrated in FIG. 20.

The techniques described and illustrated heretofore are not limited to the reduction of false alarms for LDS systems detecting small fractional absorbances. The techniques can also be applied to the reduction of noise and improvement of measurement accuracy when it is necessary to make measurements of gas concentrations that produce fractional absorbances too small to be measured accurately using conventional LDS techniques.

When measurement accuracy is important, it is not sufficient to just eliminate spurious readings by identifying circumstances where one or more of the measurements made by an LDS system cannot be relied upon, the measurements produced by the equipment must also be continuously maintained within an accuracy tolerance appropriate to the application.

When considering the laser diode to be used in systems such as those described for the claimed invention, some of the requirements placed upon this component are difficult to meet with the DFB laser diodes conventionally used in LDS systems. In particular, requirements for relatively large wavelength scanning ranges and for multiple lasers to operate at the right wavelength whilst on a common temperature stabilized mount are not readily met by DFBs. However, these requirements can be met by VCSEL laser diodes, which tune over a significantly larger wavelength range with drive current, this characteristic enabling the required wavelength scan to be realized while also facilitating adjustment of the mean output wavelength when the operating temperature is set to a common value. Long wavelength VCSEL laser diodes are virtually ideally suited for use in the claimed invention.

In the embodiments of the invention described thus far, the laser diode radiation is collected and transmitted through a monitored space and subsequently illuminates a receiver detector. However, the invention can also be beneficially employed in apparatus wherein a sample of gas to be measured is drawn into a sample measurement chamber in order to be illuminated and measured using the approaches described. This arrangement might be of particular use in applications such as process control, or where it is not practicable to transmit a measurement beam through the gas without some prior sample conditioning.

In circumstances where it is necessary to measure extremely small fractional absorbances or where optical losses mean that the system signal to noise ratio is still insufficient to achieve the required degree of measurement integrity, there may be a benefit in further extending the approaches described. In particular, instead of scanning each target gas absorption line at a single electrical frequency, each target gas absorption line could be scanned at two, non-harmonically related electrical frequencies, with measurements of the absorption by each line being based upon the magnitude of two, similar order harmonics of the non-harmonically related scanning frequencies. This process could be carried out for each absorption line being scanned and where this process is performed simultaneously, all electrical scanning frequencies employed could be chosen to be non-harmonically related.

The embodiments of the invention hereinbefore specifically described with reference to FIGS. 18 and 19 show the output from the optical detector being amplified, digitized and subsequently processed by a common digital signal processing system. This means of collecting, transmitting and measuring the laser diode radiation is a simple and cost effective implementation of the claimed invention. However, it is otherwise possible to realize the invention in apparatus wherein the magnitudes of the frequency components are determined by amplifying the detector signal and synchronously detecting the various frequency components using multiple synchronous detectors operating in parallel at different frequencies upon the same signal, the outputs from the synchronous detectors being subsequently digitized and used for the calculation of the quantity of target gas present in the measurement path as described earlier. This implementation requires a large amount of analogue electronic circuitry and does not remove the need for digitization of the signal data for further processing in the digital domain; but is a viable implementation of the claimed invention.

Figure 21:
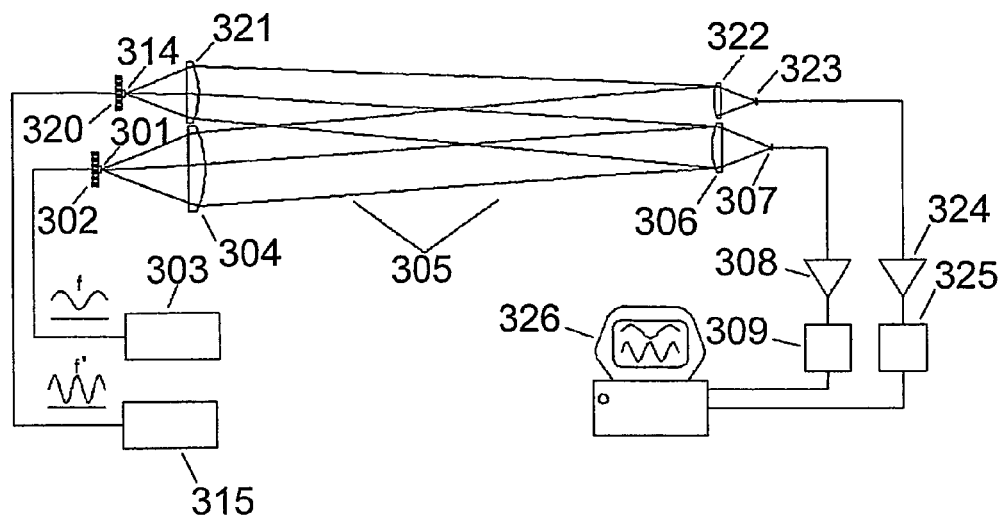
FIG. 21 shows a dual laser, dual frequency, dual wavelength laser diode gas detection or measurement system with dual transmitter optics and dual receiver optics comprising another embodiment of the present invention.

In the apparatus of FIG. 21, laser diodes 301 and 314 are respectively mounted on separate temperature stabilized mounts 302 and 320 and their radiation is separately collected and collimated by respective transmitter optical elements 304 and 321 prior to transmission through a monitored space 305. The lasers 301 and 314 are driven by respective drive circuits 303 and 315 at electrical frequencies f and f' and scanned over wavelength ranges $\Lambda_1$ and $\Lambda_2$, respectively. After passing through the monitored space 305, the two beams of collimated radiation are respectively focused onto two optical detectors 307 and 323 by optical elements 305 and 322, respectively. The electrical signals from detectors 307 and 323 are, respectively, amplified by amplifiers 308 and 324, digitized by ADCs 309 and 325, and then processed by a signal processing system 326.

Figure 22:
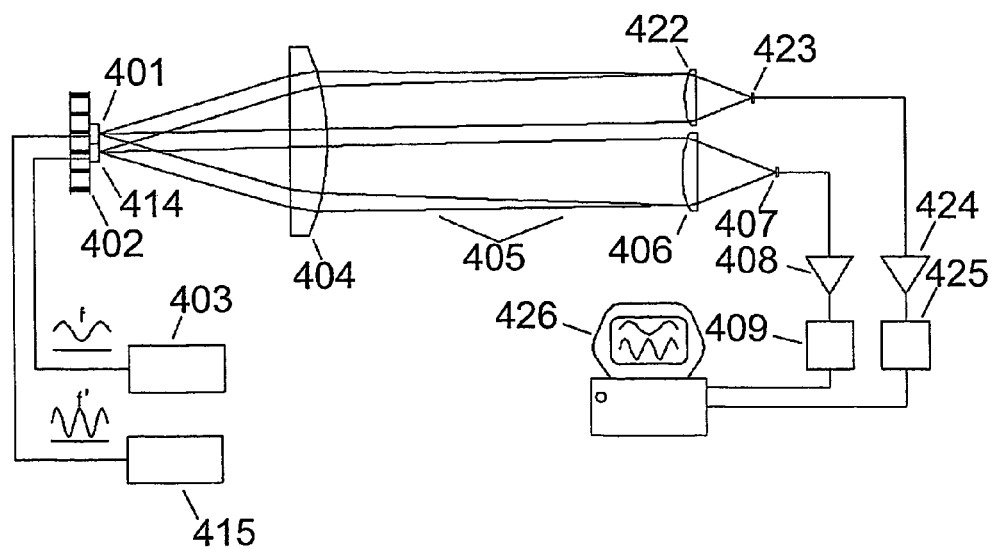
FIG. 22 shows a dual laser, dual frequency, dual wavelength laser diode gas detection or measurement system with dual receiver optics comprising another embodiment of the present invention.

In the apparatus of FIG. 22, laser diodes 401 and 414 are respectively mounted on a common temperature stabilized mount 402 and their radiation is collected and collimated by a common transmitter optical element 404 prior to transmission through a monitored space 405. The lasers 401 and 414 are driven by respective drive circuits 403 and 415 at electrical frequencies f and f and scanned over wavelength ranges $\delta\Lambda_1$ and $\delta\Lambda_2$, respectively. After passing through the monitored space 405, the two beams of collimated radiation are respectively focused onto two optical detectors 407 and 423 by optical elements 406 and 422 respectively. The electrical signals from detectors 407 and 423 are respectively amplified by amplifiers 408 and 424, digitized by ADCs 409 and 425, and then processed by a signal processing system 426.

Figure 23:
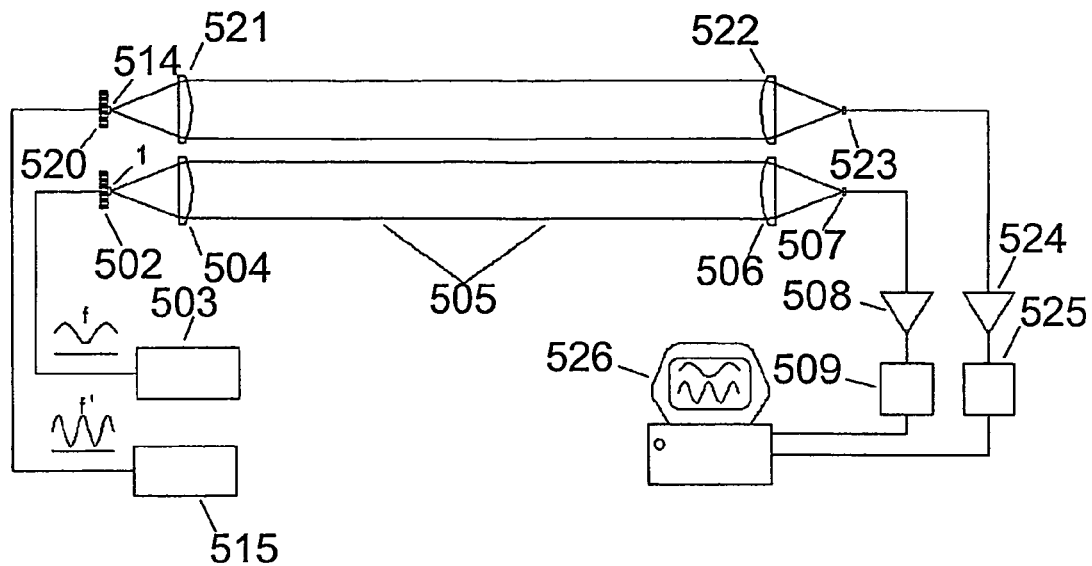
FIG. 23 shows a dual laser, dual frequency, dual wavelength laser diode gas detection or measurement system with separate optical paths for each laser diode comprising another embodiment of the present invention.

In the apparatus of FIG. 23, laser diodes 501 and 514 are respectively mounted on separate temperature stabilized mounts 502 and 520 and their radiation is separately collected and collimated by respective transmitter optical elements 504 and 521 prior to transmission through a monitored space 505. The lasers 501 and 514 are driven by respective drive circuits 503 and 515 at electrical frequencies f and f' and scanned over wavelength ranges $\delta\Lambda_1$ and $\delta\Lambda_2$, respectively. After passing through the monitored space 505, the two generally parallel beams of collimated radiation are respectively focused onto two optical detectors 507 and 523 by optical elements 506 and 522, respectively. The electrical signals from detectors 507 and 523 are respectively amplified by amplifiers 508 and 524, digitized by ADCs 509 and 525, and then processed by a signal processing system 526.

Figure 24:
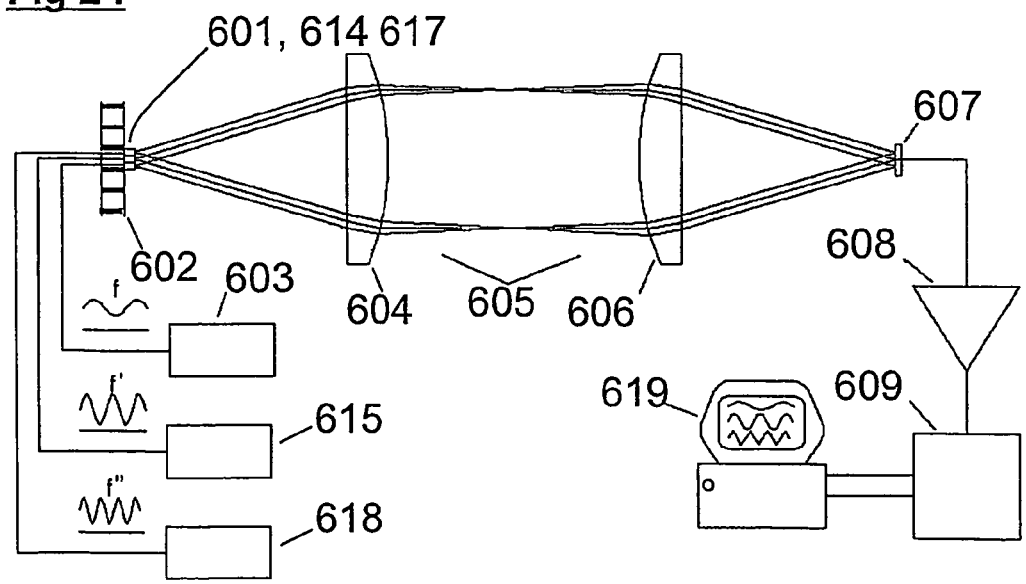
FIG. 24 shows a triple laser, triple frequency, triple wavelength laser diode gas measurement system comprising another embodiment of the present invention.
Figure 25:
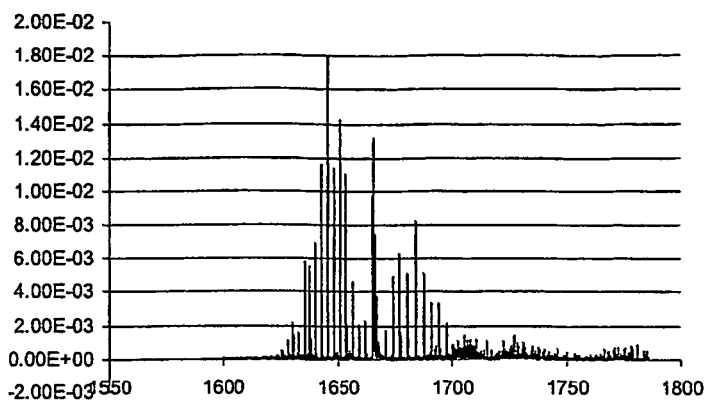
FIG. 25 shows the optical absorption spectra for 1000 ppm.m of methane between 1600 nm and 1775 nm.
Figure 26:
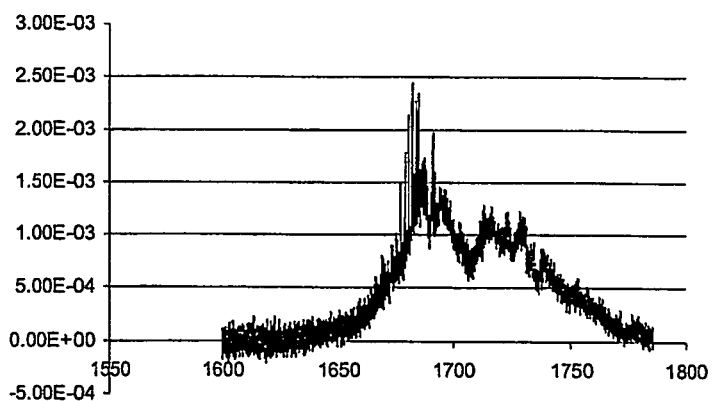
FIG. 26 shows the optical absorption spectra for 1000 ppm.m of ethane between 1600 nm and 1775 nm.
Figure 27:
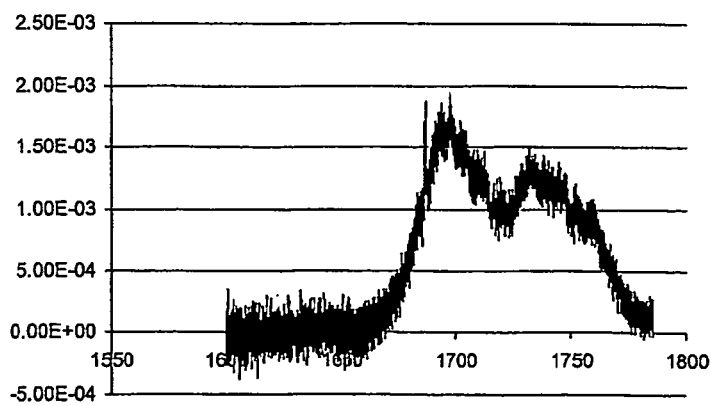
FIG. 27 shows the optical absorption spectra for 1000 ppm.m of propane between 1600 nm and 1775 nm.
Figure 28:
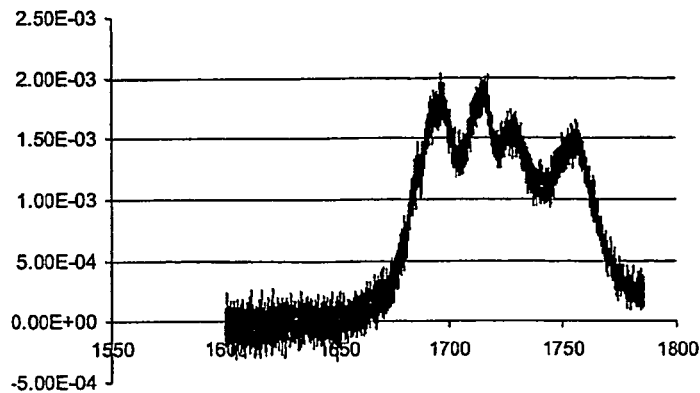
FIG. 28 shows the optical absorption spectra for 1000 ppm.m of butane between 1600 nm and 1775 nm.
Figure 29:
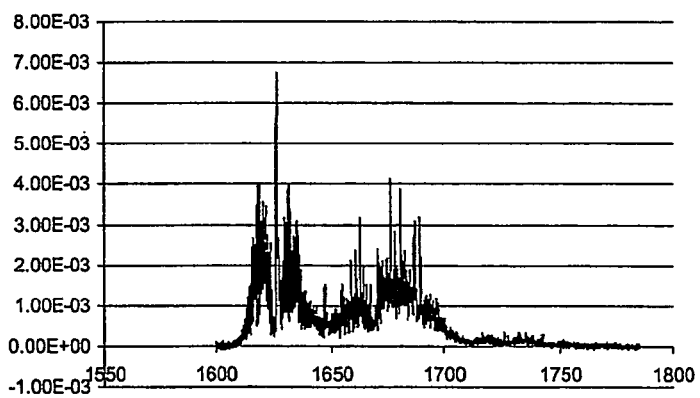
FIG. 29 shows the optical absorption spectra for 1000 ppm.m of ethylene between 1600 nm and 1775 nm.
Figure 30:
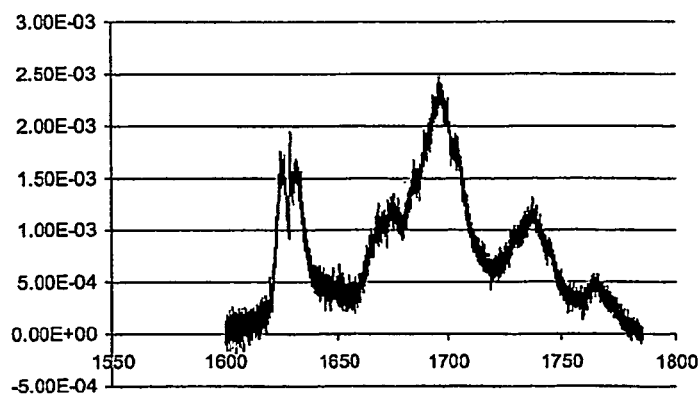
FIG. 30 shows the optical absorption spectra for 1000 ppm.m of propylene between 1600 nm and 1775 nm.
Figure 31:
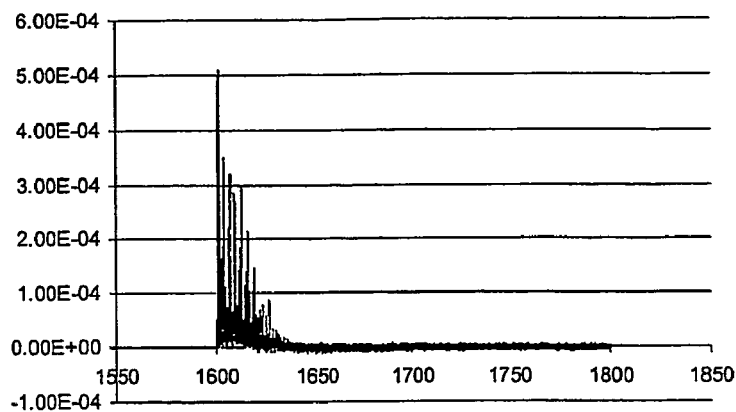
FIG. 31 shows the optical absorption spectra for 1000 ppm.m of hydrogen sulphide between 1600 nm and 1775 nm.

The requirement to maintain measurements continuously within a prescribed accuracy tolerance whilst measuring gases which produce small fractional absorbances can be met by apparatus as shown in FIG. 24, comprising another embodiment of the invention. The apparatus of FIG. 24 has three laser diodes 601, 614 and 617 operating at mean wavelengths $\Lambda_1$, $\Lambda_2$ and $\Lambda_3$, driven by laser drive circuits 603, 615 and 618, scanning ranges $\delta\Lambda_1$, $\delta\Lambda_2$ and $\delta\Lambda_3$ at electrical frequencies f, f' and f''. The outputs from the laser diodes 601, 614 and 617 are collimated by a transmitter optical element 604, passed through a monitored space 605 and then focussed onto a receiver detector 607 by a receiver optical element 606. The signal from the detector 607 is amplified by an amplifier 608, digitized digitized by ADC 609 and processed by a signal processing system 626.

The quantity of target gas present in the monitored space 605 is proportional to the normalized amplitude of frequency components $f_1$, $f_2$ and $f_3$ produced by absorption of optical radiation by target gas when each laser's wavelength scans across its respective target gas absorption line. In order to achieve the best results, the use of quantities $Q_1$, $Q_2$ and $Q_3$ for calculation of the amount of gas in the monitored space should be in combination with results for previous measurements, using rules dependent upon the quality of agreement between the quantities. These rules and their intended effects are as follows—

RB1 If $Q_1$, $Q_2$ and $Q_3$ are in close agreement, a large fraction of the average of $Q_1$, $Q_2$ and $Q_3$ is added to a balancing fraction of the running average of previous results for calculating the quantity of gas present in the monitored space 605. This enables the output from the apparatus to quickly track changes in the quantity of target gas present in the monitored space when confidence in all of the most recent measurements is high.

RB2 If either $Q_1$ and $Q_2$, or $Q_2$ and $Q_3$, or $Q_1$ and $Q_3$ are in close agreement with each other and the running average of previous results, the quantity which is not in close agreement is rejected whilst a large fraction of the average of the remaining quantities is added to a balancing fraction of the running average of previous results for calculating the quantity of gas present in the monitored space 605. This prevents measurements in which confidence is not sufficiently high from affecting the output from the apparatus; whilst allowing measurements in which there is high confidence to contribute to keeping the output from the apparatus accurate and up to date.

RB3 If $Q_1$, $Q_2$ and $Q_3$ are in reasonable but not close agreement with each other and the running average of previous results, a lesser fraction of the average of $Q_1$, $Q_2$ and $Q_3$ is added to a larger balancing fraction of the running average of previous results for calculating the quantity of gas present in the monitored space 605. This enables the output to take account of the most recent measurements whilst limiting the impact that any potential errors in these measurements might have upon the output of the apparatus.

RB4 If $Q_1$, $Q_2$ and $Q_3$ are in reasonable but not close agreement with each other but not in close or reasonable agreement with the running average of previous results, a still lesser fraction of the average of $Q_1$, $Q_2$ and $Q_3$ is added to a still larger balancing fraction of the running average of previous results for calculating the quantity of gas present in the monitored space 605. This enables the output to contingently take account of the most recent measurements whilst further limiting the impact that any potential errors in these measurements might have upon the output of the apparatus until measurements in which there is greater confidence are available.

RB5 If only one of the quantities $Q_1$, $Q_2$ or $Q_3$ is in close agreement with the running average of previous results, the other quantities are rejected and a fraction of the remaining quantity is added to a larger balancing fraction of the running average of previous results for use in the calculation of the quantity of gas present in the monitored space 605. This enables the output of the apparatus to be kept moving in the right direction in the event of there being low confidence in two of the most recent measurements. (This situation should not be common if the system is working correctly.)

RB6 If $Q_1$, $Q_2$ and $Q_3$ are in poor agreement with each other and the running average of previous results, $Q_1$, $Q_2$ and $Q_3$ are rejected and the calculation of the quantity of gas present in the monitored space 605 is based solely upon the running average of previous results, the balancing fraction being set to unity. This enables spurious readings due to measurements in which confidence is low to be effectively eliminated, whilst maintaining the output from the apparatus at the most recent level in which confidence is acceptably high. (The use of a system configuration as shown in FIG. 24 should make the probability of such a condition very low and if this condition persists it is likely that there is a problem which needs to be signalled to the user.)

The above rules RB1 to RB6 for the use of quantities $Q_1$, $Q_2$ and $Q_3$ in combination with the running average of previous results can be further refined by adjusting the fractions of recent and previous results used in proportion to the quality of agreement between them, such adjustment depending upon where in the agreement quality range for a particular rule the results fall.

The means of collection and collimation of the optical radiation from the laser diode(s) need not be limited to simple optical elements. The optical elements used for this purpose can comprise a number of separate optical elements combined to perform the required function of laser diode radiation collection, collimation and transmission through the monitored space. Furthermore, these optical elements need not be limited to the free-space optical elements shown. The radiation from the laser diode(s) can be coupled into fibre-optic cable(s) and carried to one or more optical elements that will collimate and transmit the radiation through the monitored space.

Readings or measurements from gas detectors or related instrumentation are output by various means, these mainly depending upon how and by what the readings or measurements are to be used. The means of output for readings or measurements from the claimed invention could include an analogue electrical signal proportional to the concentration or quantity of gas, a digital electronic signal conforming to a defined protocol and containing numerical data conveying the concentration or quantity of gas, a numerical representation of the concentration or quantity of gas upon a display and the opening or closing of relays at prescribed concentrations or quantities of gas.

Hazardous Gas Detection

When considering the design of an ideal hazardous gas detector for the petrochemical industry meeting the requirements outlined hereinbefore, the use of conventional LDS techniques presents the designer with three key problems. First, the wavelength tuning range of most laser diodes is only a few nanometres. This relatively small tuning range is insufficient to enable measurements to be made on a large number of gas species. Second, the LDS technique is only appropriate for making measurements of gases with narrow, well-resolved absorption features or lines. The gas molecules which exhibit narrow, well-resolved absorption features are small, simple molecules, but butane and propylene are not small, simple molecules and their absorption spectra do not contain narrow, well-resolved absorption features or lines. The third key problem arises from the fact that hydrogen sulphide has a Threshold Limit Value (TLV) of 10 ppm and only exhibits weak absorption in the wavelength regions accessible with room temperature laser diodes. In the 1550 nm to 1625 nm region that is best suited to the detection of hydrogen sulphide, 10 ppm.m of $H_2S$ will produce a maximum fractional absorbance of just $4 \times 10^{-6}$, which is too small to be detected reliably enough for use in safety applications.

Close inspection of the absorption spectra of methane, ethane, propane, butane, ethylene, propylene and hydrogen sulphide shown respectively in FIGS. 24 to 30 reveals that over the range 1600 nm to 1785 nm neither butane nor propylene possess absorption features suitable for conventional LDS measurements; whilst propane only possesses a single well-resolved feature, at 1686.4 nm. Also, there is no wavelength region where it is possible to make measurements of all of the flammable gases of interest plus hydrogen sulphide.

Figure 32:
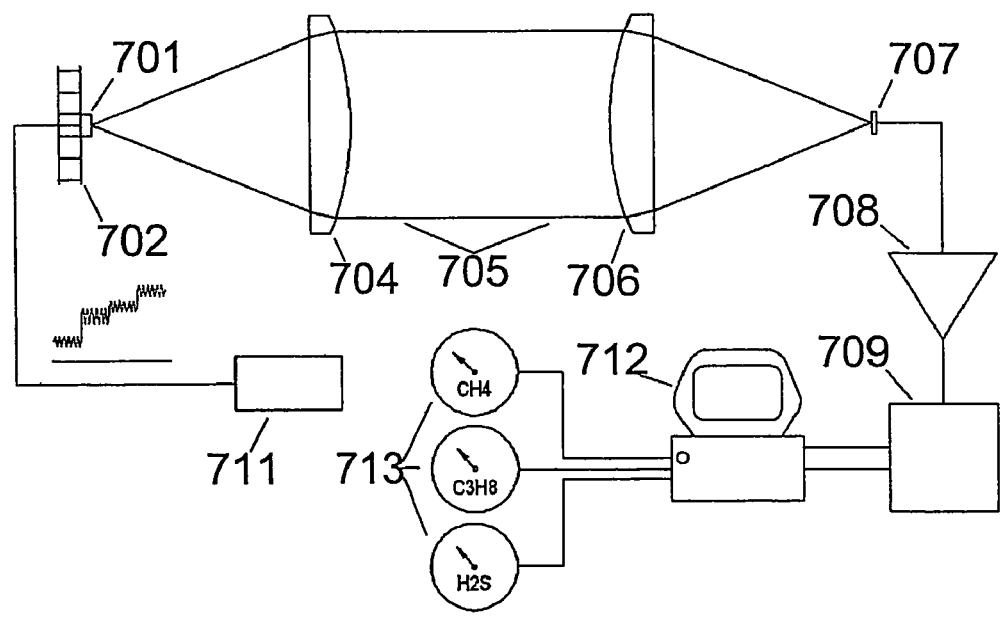
FIG. 32 shows a hazardous gas detector comprising another embodiment of the present invention.
Figure 33:
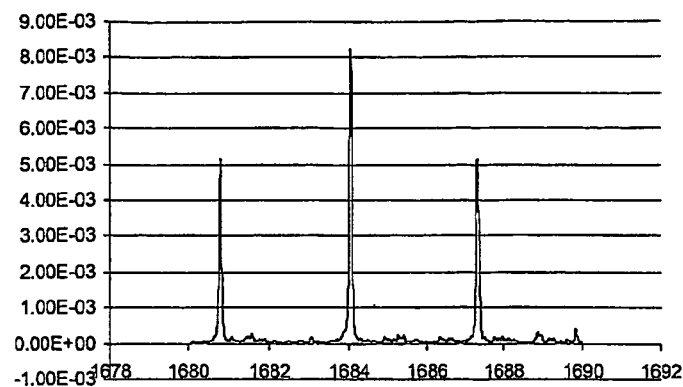
FIG. 33 shows the optical absorption spectra for 1000 ppm.m of methane between 1680 nm and 1690 nm.
Figure 34:
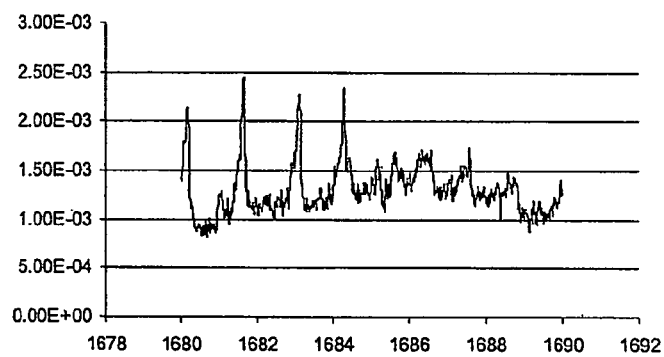
FIG. 34 shows the optical absorption spectra for 1000 ppm.m of ethane between 1680 nm and 1690 nm.
Figure 35:
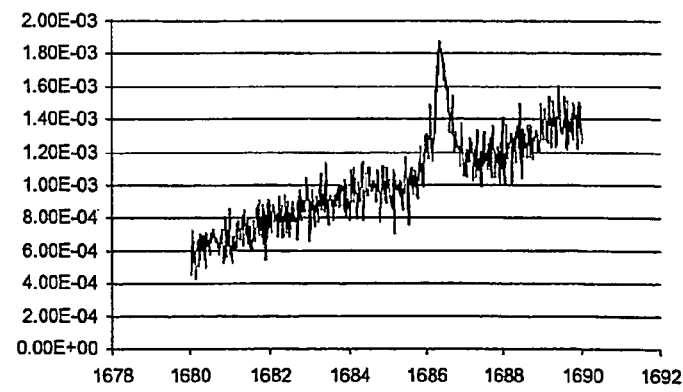
FIG. 35 shows the optical absorption spectra for 1000 ppm.m of propane between 1680 nm and 1690 nm.

FIG. 32 illustrates a hazardous gas detector according to the present invention that addresses these problems. Referring therefore to FIG. 32, a laser diode 701 is mounted on a mount 702 and energized by a drive circuit 711.

When considering the laser diode to be used in apparatus such as that of FIG. 32, some of the requirements placed upon this component are difficult to meet with the distributed feedback (DFB) laser diodes conventionally used in LDS systems. In particular, requirements for relatively large wavelength scanning ranges are not readily met by DFB lasers. However, these requirements can be met by a vertical cavity surface emitting laser (VCSEL) laser diode, which tunes over a significantly larger wavelength range with drive current. Long wavelength VCSEL laser diodes are therefore preferred in the present invention.

The VCSEL 701 has a nominal wavelength of 1685.5 nm and is capable of being current tuned over the range 1684 nm to 1687.5 nm, thus providing access to the strong absorption lines or features of methane at 1684 nm and 1687.3 nm, ethane at 1684.3 nm, propane at 1686.4 nm and ethylene at 1687.0 nm. (See FIGS. 32 to 35.) The output radiation from the laser diode 701 is collected and collimated by an optical element 704, the resulting beam being transmitted through a monitored space 705 to a receiver optical element 706, which focuses the received radiation onto a detector 707. The signal from the detector 707 is amplified by an amplifier 708 and digitized by ADC 709, and then processed by a signal processing system 712 to determine which gases, if any, are present in the monitored space and in what quantities. The determination of which flammable gases, if any, are present in the monitored space is based upon the known characteristics of the absorption lines and features of methane, ethane, propane and ethylene which the detector scans. The quantities of each gas calculated to be present in the monitored space are output separately by an output interface 713.

Figure 37:
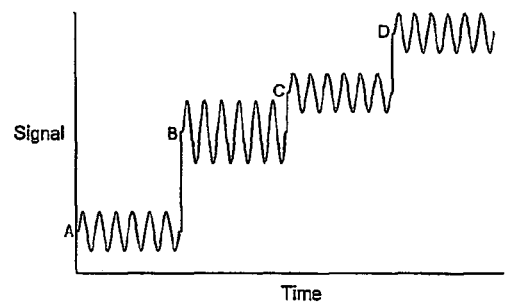
FIG. 37 illustrates a drive current for application to the laser diode of the detector of FIG. 32.

FIG. 37 illustrates a drive current that may be applied to the laser diode 701 by the drive circuit 711. The bias component of the current sequences between levels A, B, C and D, levels chosen to operate the laser diode 701 at mean wavelengths close to the different target gas absorption lines and features at 1684.3 nm, 1686.4, 1687.0 nm and 1687.3 nm, respectively. The amplitudes of the sinusoidal current components which scan the laser diode's wavelength across each target gas absorption line or feature are independently optimized for each absorption line or feature. The amplitudes of both the bias and sinusoidal components are carefully chosen to avoid scanning the laser across the absorption lines of atmospheric water vapor at 1684.23 nm, 1687.07 nm and 1685.92 nm.

Figure 38:
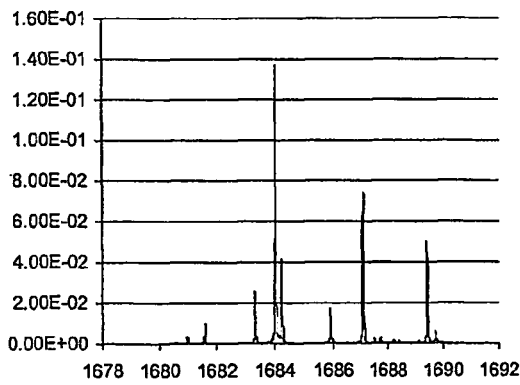
FIG. 38 shows the optical absorption spectra for a 100 metre path through the atmosphere at 100% RH, 30° C., between 1680 nm and 1690 nm.

The strong methane line at 1684 nm is not used in this embodiment of the invention because this wavelength is very close to a strong water vapour absorption line which has the potential to interfere with measurements made along open atmospheric paths (See FIG. 38.).

There are two processes performed by the signal processing system 712 of FIG. 32 which call for further explanation. These processes are the determination of which gases are present in the monitored space 705 and the estimation of the amount of hydrogen sulphide present.

First, the determination of which gases are present in the monitored space 705 is based upon analysis of the set of measurement results for the laser operating at each mean wavelength close to the strong absorption lines or features of ethane, propane, ethylene and methane respectively. In determining the gas or gases present, the analysis needs to take account of the fact that ethane and ethylene have multiple absorption features in the 1684 nm to 1687.5 nm wavelength range.

The analysis of the measurement results for scans produced at bias currents A, B, C and D can proceed by four steps as follows. First, the signals for periods corresponding to bias currents A, B, C and D are separately windowed and Fourier transformed. Next, the harmonic frequency components in each Fourier transform are normalized with respect to the amplitude of the fundamental, wavelength scanning frequency component. Then the relative amplitude patterns of the measured harmonic components are compared with the known relative amplitude patterns for the harmonic components produced by each target gas at each bias current level. And finally the results of the comparison of the patterns at each bias current level are logically and proportionately combined to identity the gas or gases present in the monitored space.

Since the relative amplitude pattern for each target gas is known for each bias current level, all comparison results for all bias levels can make a contribution to the identification of the gas or gases present in the monitored space 705. The absence of harmonics in a scan at a mean wavelength at which a gas is known not to absorb can contribute to the confirmation of the presence of a particular candidate gas. By similar reasoning, the presence of harmonics in a scan at a mean wavelength at which a gas is known not to absorb can contribute to the elimination of a particular candidate gas.

Having identified the flammable gas or gases present in the monitored space 705, the quantity of each gas present can be calculated. This calculation uses the known absorption cross-sections of each identified gas and Beers law to calculate the amount of gas required to produce normalized harmonic frequency components of the sizes measured.

Turning now to the question of estimating the quantity of hydrogen sulphide present in the monitored space 705, this can be derived from the quantity of methane measured in the monitored space and knowledge of the relative concentrations of methane and hydrogen sulphide in the solution gas of a particular oil or gas field.

Estimation of the amount of hydrogen sulphide present in the monitored space 705, rather than an attempt to measure, is justified for a number of reasons. First, for sour oil or gas fields, the relative concentrations of methane and hydrogen sulphide in the solution gas of that field are known. Second, when solution gas leaks from vessels containing oil or gas from a sour field, the relative concentrations of methane and hydrogen sulphide in the leaking gas are the same as those in the solution gas inside the vessel. Third, the methane and hydrogen sulphide in solution gas are intimately mixed and do not separate or stratify when they disperse into the area surrounding a leaking vessel. And fourth, any changes in the amount of hydrogen sulphide present in the solution gas of an oil or gas field are very gradual.

The mathematics for calculating an estimate of the amount of hydrogen sulphide present in the monitored space 705 based upon the measured quantity of methane is relatively simple. A single coefficient $K_{H2S}$ can be calculated, based upon the known relative concentrations of methane and hydrogen sulphide in the field's solution gas, where $$K_{H2S} = [\text{hydrogen sulphide}]/[\text{methane}]$$

By way of example, if a hazardous gas detector according to the present invention detects 4,800 ppm.m of methane when the solution gas for the field is known to contain 960,000 ppm methane and 10,000 ppm hydrogen sulphide, the estimated quantity of hydrogen sulphide present would be:

$$H_2S = 4,800 \times K_{H2S}$$
$$= 4,800 \times 10,000/960,000$$
$$= 50 \ ppm.m$$

For a monitored space that is 10 metres long, the claimed detector would indicate an average hydrogen sulphide concentration of 5 ppm, which is 50% of the TLV for hydrogen sulphide.

In order to facilitate the estimation of the amount of hydrogen sulphide present in the monitored space as described for the claimed invention, means is provided to inform the signal processing system 712 of the calculated $K_{H2S}$ coefficient for solution gas at or from a particular field. By making it possible to update the $K_{H2S}$ coefficient as and when required, any gradual changes in the sourness of the solution gas of a particular field can be accommodated.

There are a number of benefits associated with the estimation of the amount of hydrogen sulphide as described above— a) It enables a single hazardous gas detector to be produced that is capable of providing warnings about both flammable and toxic gas hazards typically found at petrochemical facilities.
b) Detection of methane using LDS techniques is significantly easier than detection of hydrogen sulphide using LDS techniques. In particular, the optical absorption lines of methane accessible using room temperature laser diodes are at least an order of magnitude stronger than the accessible optical absorption lines of hydrogen sulphide.
c) For the vast majority of oil or gas fields, methane is the principal constituent of solution gas. Detecting the principal constituent of solution gas increases the probability of early detection of any leak of solution gas.
d) Unlike conventional flammable gas detectors, the present invention is capable of identifying the flammable gas present in the monitored space and only signalling an estimate of the amount of hydrogen sulphide present if this gas is methane. Small, background concentrations of flammable gases or vapours that are common-place at petrochemical facilities but that are not hazardous will not give rise to warnings about a hydrogen sulphide hazard.

The resulting hazardous gas detector is considerably simpler than an LDS based detector capable of directly measuring both methane and hydrogen sulphide. This simplicity is beneficial because it improves the reliability and robustness of the gas detector whilst simultaneously reducing its manufacturing cost. Furthermore, if the operators of petrochemical facilities only have to install a single type of gas detector, this will reduce the installation and operation costs of their gas detection systems.

There are a number of ways in which the readings of the claimed hazardous gas detector can be output. The apparatus may include multiple analogue or digital displays, each displaying the quantity of a particular gas. There may be a display screen with values presented for each of the gases that can be detected. The apparatus may deliver multiple analogue electrical outputs, each producing a signal proportional to the quantity of a particular gas. A digital electronic signal conforming to a defined protocol and containing numerical data may be provided to convey the concentration or quantity of each gas. Otherwise readings may effect the opening or closing of relays at prescribed flammable gas or hydrogen sulphide concentrations.

As with other embodiments of the present invention, the means of collection and collimation of the optical radiation from the laser diode need not be limited to the simple optical element shown in FIG. 32. The optical element used for this purpose can comprise of a number of separate optical elements combined to perform the required function of laser diode radiation collection, collimation and transmission through the monitored space. Furthermore, these optical elements need not be limited to the free-space optical elements shown. The radiation from the laser diode can be coupled into fibre-optic cable and carried to one or more optical elements which will collimate and transmit the radiation through the monitored space.

Figure 39:
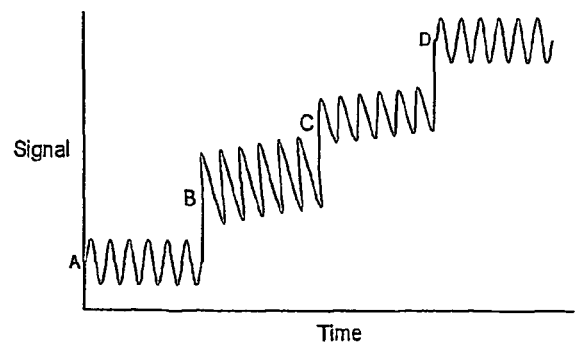
FIG. 39 illustrates another form of drive current that may be applied to the laser diode of the detector of FIG. 32.

FIG. 39 shows a drive current whereby the reliability of identification or discrimination of gases such as propane and ethylene can be further enhanced. A slope is applied to the bias component of the drive current when scanning over the wavelength regions which contain their strongest absorption features. By this means the mean wavelength of the laser diode is gradually swept through the region of the absorption feature of interest. The pattern of harmonic components produced during a sweep will be different when absorption features with different shapes are scanned. These differences can be used to discriminate propane from ethylene despite the presence of absorption features at common wavelengths.

Figure 36:
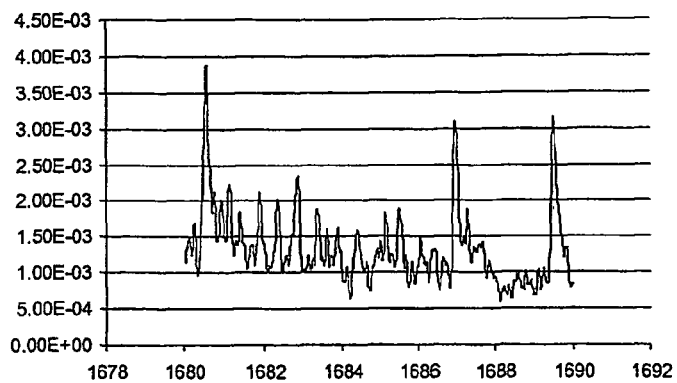
FIG. 36 shows the optical absorption spectra for 1000 ppm.m of ethylene between 1680 nm and 1690 nm.

Those skilled in the science will appreciate that the application of a slope to the bias current could be extended to encompass the entire wavelength range 1684 nm to 1687.3 nm, with the net effect of enabling an absorption spectrum for the monitored space to be determined for the range 1684 nm to 1687.3 nm. This spectrum would include measurements of absorption by atmospheric water vapour at 1684.23 nm, 1687.07 nm and 1685.92 nm. The disadvantage of capturing a spectrum for the entire wavelength range 1684 nm to 1687.3 nm is that the only regions of significant interest are in and around the gas absorption lines and features at 1684.3 nm, 1686.4, 1687.0 nm and 1687.3 nm. By spending time measuring regions of no or limited interest, the time spent measuring the regions of primary interest is reduced, with the net effect of degrading overall system signal to noise ratio. It is for this reason that the laser current drive waveforms in preferred embodiments of the claimed invention cause the laser to scan discrete, non-continuous wavelength regions, as will be understood from FIGS. 36 and 38.

While it is preferred in a hazardous gas detector according to the present invention to use a VCSEL laser capable of scanning the range 1684 nm to 1687.5 nm, as it is capable of detecting most flammable gases present at petrochemical facilities, this is not the only way in which the present invention can make use of the technique described for estimation of the quantity of hydrogen sulphide present n the monitored space. Any LDS based gas detector capable of detecting methane with high sensitivity and specificity could be used as the basis of a combined methane and hydrogen sulphide detector employing the estimation technique described for the claimed invention. Such an LDS based gas detector need not use a VCSEL laser and could operate at any wavelength where methane exhibits sufficient optical absorption to enable sensitive measurements to be made.

It should be noted that the apparatus of FIG. 32 may be modified so that, instead of transmitting laser diode radiation directly through a monitored space, a sample of gas from an area to be monitored is drawn into a sample measurement chamber in order to be illuminated and measured using the methods described.

Further, rather than the output from the optical detector 707 being amplified, digitized and subsequently processed by a digital signal processing system, it is possible to realize the claimed invention in an apparatus where the magnitudes and phases of the frequency components are determined by amplifying the detector signal and synchronously detecting the various frequency components using multiple synchronous detectors operating in parallel at different frequencies upon the same signal. The outputs from the synchronous detectors would subsequently be digitized and used for the calculation of the quantity of target gas present in the monitored space as described earlier.

The hazardous gas detector hereinbefore described with particular reference to FIGS. 24 to 38 makes use of the fact that the hydrogen sulphide in sour solution gas is intimately mixed with natural gas, which is predominantly methane, and that the ratio of hydrogen sulphide to methane in the solution gas of a particular oil or gas field is known. By specifically detecting or measuring the amount of methane in a monitored path, and using the known ratio of hydrogen sulphide to methane for a particular field's solution gas, an estimate of the amount of hydrogen sulphide present in the monitored path is produced, this estimate being used to determine whether or not the amount of hydrogen sulphide present represents a toxic hazard.

This form of hazardous gas detector provides warnings about both the flammable and toxic gas hazards presented by a leak of the solution gas from a particular, known oil or gas field. However, it relies for its operation upon knowledge of the ratio of hydrogen sulphide to methane in the solution gas that it is detecting. Facilities that receive and process oil or gas from a number of different sources will not have a single, known ratio of hydrogen sulphide to methane for the solution gas. Indeed, some of the oil or gas handled by such facilities may be sweet, there being no hydrogen sulphide in the solution gas. Consequently, the hazardous gas detector of FIG. 32 may be of limited use at facilities receiving oil or gas from a wide variety of different sources.

However, such a detector can be modified to detect both flammable and toxic gas hazards associated with leaking solution gas at facilities receiving oil or gas from a number of different sources. This can be done by providing a transmitter comprising two laser diodes, one operated at wavelengths to scan absorption lines of flammable gases including methane, ethane and propane, the other operated at a wavelength to scan an absorption line of hydrogen sulphide.

Detection or measurement of gases such as methane at flammable concentrations is sufficiently easy using laser diode spectroscopy techniques that it can be performed reliably using a single laser diode. However, for reasons hereinbefore set forth, detection or measurement of hydrogen sulphide at toxic concentrations cannot be performed reliably using a single measurement. Any such attempt would result in a false alarm rate unacceptably high for safety applications.

Testing for both hydrogen sulphide and methane etc overcomes this problem. If sour solution gas is leaking then the hydrogen sulphide will be detected by absorption measurements made at the chosen hydrogen sulphide absorption line wavelength and methane will be detected by absorption measurements made at the chosen methane absorption line wavelength. Only if both hydrogen sulphide and methane are detected at sufficient concentrations can there genuinely be a toxic gas hazard present due to hydrogen sulphide. If the amount of methane measured in the monitored path is less than that which would be known to be present in the most sour solution gas that a particular facility might handle, then the hydrogen sulphide measurement must be false, and no toxic gas alarm is signalled.

The false alarm rejection strategy here is based upon the fact that whilst it is possible for solution gas either to contain or not to contain hydrogen sulphide (depending upon its source) solution gas always contains a very significant quantity of methane.

A further improvement can be secured from knowing the minimum ratio of methane to hydrogen sulphide for a given facility—which corresponds to the most sour oil or gas that a facility will ever handle or process. The amount of hydrogen sulphide present in oil or gas needs to be known by the operators of oil and gas facilities because it affects where and how it can be handled and processed, and most importantly, the cost of processing the oil or gas for subsequent sale and use. Using the known minimum ratio of methane to hydrogen sulphide for a given facility, the improved hazardous gas detector can be arranged to calculate the minimum amount of methane that needs to be present for a detected quantity of hydrogen sulphide to be the genuine consequence of a solution gas leak.

High Integrity Gas Detection.

It will be recalled from earlier discussion of FIG. 8 that the output of a detector shows a deviation from a simple sinusoidal waveform, caused by absorption of optical radiation when the wavelength of the laser diode scans through the region of the absorption line of the target gas. The optical absorption by the target gas introduces an absorption feature whenever the wavelength of the laser crosses the region of the absorption line, which in FIG. 8 occurs approximately half way up the positive excursion of the modulation cycle. Various methods can be used to measure the relative size of the absorption feature and to subsequently determine the amount of target gas in the monitored space, the most popular of which is synchronous detection and measurement of the second and/or third harmonics. Alternatively, the signal can be digitized as described with reference to FIG. 1 and then processed using digital signal processing techniques to measure the magnitude of the various frequency components in the detector signal and determine the amount of gas present in the monitored space.

Figure 40:
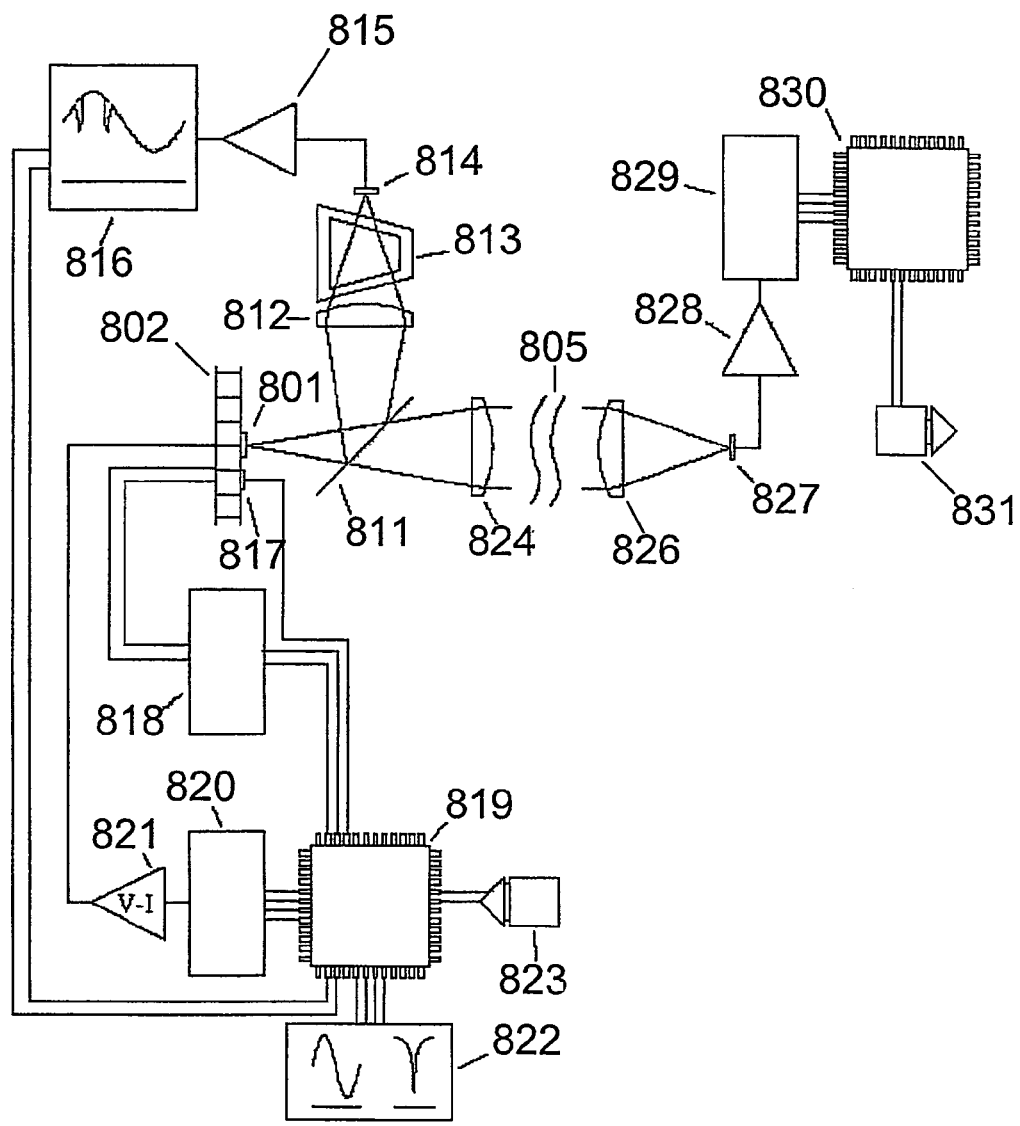
FIG. 40 shows a high integrity gas detector comprising another embodiment of the present invention.

A high integrity gas detector comprising another embodiment of the present invention is shown in FIG. 40. A laser diode 801 is driven by a laser diode drive current synthesizer comprising a microprocessor 819, waveform memory 822, a Digital-to-Analogue-Converter (DAC) 820 and a voltage-to-current (V-I) converter 821. The laser diode 801 is mounted on a temperature stabilized mount 802 which is itself driven by a temperature stabilization drive circuit 818, with feedback of the temperature of the mount 802 being provided by a temperature sensing element 817. The laser diode drive current synthesiser synthesizer operates under the control of the microprocessor 819, which uses waveform data stored in the waveform memory 822 together with drive control software to send a sequence of digital values to the DAC 820, which in turn converts the digital values into their corresponding voltages. The voltages output by the DAC 820 are filtered and turned into a current by the V-l converter 821, the resulting current waveform corresponding to the desired laser diode drive current waveform, including bias and scanning components.

The output from the laser diode 801 is split into two fractions by a beam-splitter 811. One fraction is passed through a retained target gas sample 813 and concentrated onto an optical detector 814 by an optical element 812. The other fraction is collimated by an optical element 824 and transmitted through a monitored space 805.

The signal from the optical detector 814 is amplified by an amplifier 815 and converted into a sequence of corresponding digital values by an Analogue-to-Digital-Converter (ADC) 816. Because the optical signal reaching the detector 814 has been passed through a substantial retained sample of the target gas, the detector signal contains one or more significant absorption features produced by absorption of the optical radiation from the laser diode when its wavelength corresponds to that of the absorption line(s) of the target gas. The digitized detector signal is processed by the microprocessor 819 to determine the position, width and shape of the absorption line(s) of the target gas with respect to the wavelength scanning waveform. This information is then used by the microprocessor to adjust the amplitude of the bias and scanning components along with the laser diode operating temperature in order to maintain the chosen target gas absorption line(s) with constant position and width with respect to the wavelength scanning waveform.

The optical radiation passing through the monitored space 805 is collected and concentrated onto an optical detector 827 by an optical element 826. The electrical signal from the detector 827 is amplified by an amplifier 828 and converted into a sequence of digital values corresponding to the detector signal by an Analogue-to- Digital-Converter (ADC) 829. The digitized signal is then processed by a microprocessor 830 to determine the relative amplitude of any absorption feature with position and width corresponding to those known to be maintained by the transmitter. The relative amplitude of any such absorption feature is then used to calculate the quantity of target gas in the monitored space, this quantity being output by a receiver output interface 831.

The optical radiation passing through the monitored space 805 is collected and concentrated onto an optical detector 827 by an optical element 826. The electrical signal from the detector 827 is amplified by an amplifier 828 and converted into a sequence of digital values corresponding to the detector signal by an Analogue-to-Digital-Converter (ADC) 829. The digitized signal is then processed by a microprocessor 830 to determine the relative amplitude of any absorption feature with position and width corresponding to those known to be maintained by the transmitter. The relative amplitude of any such absorption feature is then used to calculate the quantity of target gas in the monitored space, this quantity being output by a receiver output interface 831.

The transmitter includes an interface 823, by which either an operator or a control system can instruct the transmitter to simulate the presence of a nominated quantity of target gas in the monitored space 805. This simulation is performed under the immediate control of the microprocessor 819, which has access to data detailing the position, width and shape of the target gas absorption line(s) with respect to the wavelength scanning waveform. The microprocessor 819 uses this data in conjunction with scanning waveform data and equations describing the amount of absorption produced by a given quantity of target gas to calculate a sequence of digital values which when turned into a current by the DAC 820 and the V-I converter 821, will produce a laser drive current waveform including a replica absorption feature, the position, width, shape and size of the replica absorption feature corresponding to that which would be produced by the nominated quantity of target gas being present in the monitored space. In order for the operator or control system to have the necessary control of any gas simulation test, the transmitter interface 823 is also capable of receiving instructions concerning the duration of any gas simulation test and/or instructions to cease any test.

The benefits of actively maintaining the position and width of the absorption line(s) of the target gas with respect to the wavelength scanning waveform are as follows— a) The largest potential source of detection or measurement drift in a system using LDS techniques is associated with changes in the operating wavelength of the laser diode with temperature or ageing. By actively maintaining the position and width of the target gas absorption line with respect to the wavelength scanning waveform, this largest form of drift is effectively eliminated.

b) The amount of absorption produced by a particular quantity of target gas at a wavelength corresponding to one of its absorption lines is a fixed property of the gas. By maintaining the position and width of the target gas absorption line with respect to the wavelength scanning waveform, all that the receiver has to do in order to detect or measure the quantity of target gas in the monitored space is to measure the relative size of any absorption feature with position and width corresponding to those known to be actively maintained with respect to the wavelength scanning waveform. This is a relatively simple measurement for the receiver to make.

c) The retained sample of the target gas is only used to provide information upon the position, shape and width of the target gas absorption line(s), these being fixed properties of the target gas. Loss of target gas from the retained sample may change the amount of optical radiation absorbed when radiation from the laser diode is passed through the retained sample, but it will not change the position, shape and width of the target gas absorption line(s). When used in this manner, small leaks from the retained sample do not lead to the problems that are associated with use of the retained sample as a quantitative gas calibration standard.

Figure 41:
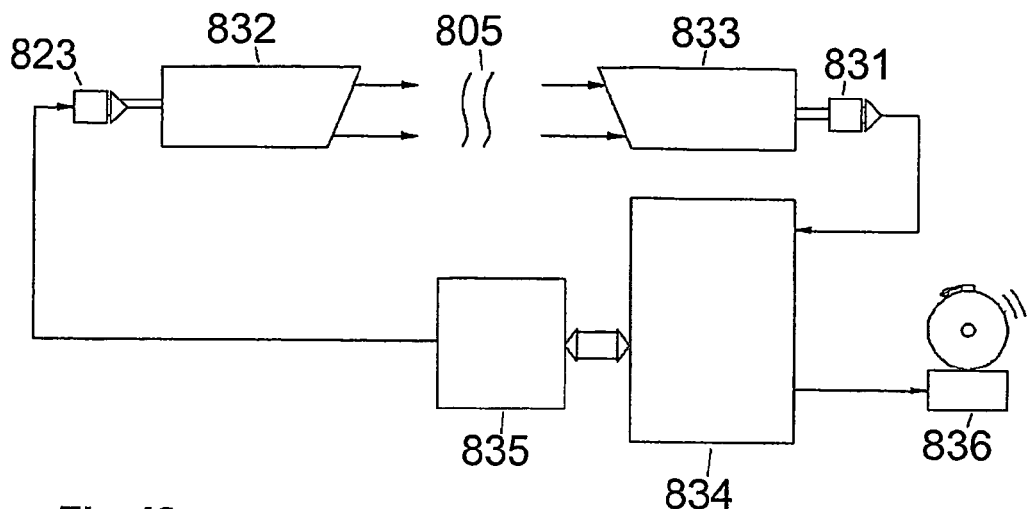
FIG. 41 illustrates the use of the detector of FIG. 40 in a high integrity gas detection system.

The use of the detector of FIG. 40 as part of a high integrity gas detection system according to the present invention is illustrated by FIG. 41. The system illustrated in FIG. 41 includes a transmitter 832 in communication with a system status monitoring and test unit 835 by way of the transmitter interface 823. The optical radiation from the transmitter 832 passes through the monitored space 805 to a receiver 833. The output gas reading from the receiver 833 is signalled to a gas detection system controller 834 by way of the receiver output interface 831. During normal operation, the gas detection system controller 834 continuously monitors the gas reading output from the gas detector of the claimed invention, this reading corresponding to the quantity of target gas present in the monitored space 805. In the event of a significant quantity of hazardous gas being detected and a corresponding signal output by the receiver output interface 831, the gas detection system controller 834 raises an appropriate warning via an alarm 836 and initiates any pre-programmed executive actions.

Maintenance of the safety integrity of the gas detection system is performed under the control of the system status monitoring and test unit 35, the necessary testing either being initiated by an operator or by a software programme running on the system status monitoring and test unit.

In order to provide confidence in the ability of the gas detection system to function correctly in the event of a hazardous gas leak, it is necessary to conduct tests which simulate a gas hazard being present in the monitored space 805 and verify the correct operation of the gas detector and gas detection system controller 834 in response to this simulated hazardous condition. The features provided in the gas detector of the claimed invention make conducting such tests considerably easier than would be the case for conventional gas detectors.

The procedure for performing the gas detection system integrity test is essentially as follows— a) The system status monitoring and test unit 835 is instructed by an operator or software running on the unit to perform a system integrity test upon the gas detection system.

b) The system status monitoring and test unit 835 communicates with the gas detection system controller 834, notifying it that a test is about to be performed and which gas detectors are to be tested.

c) The gas detection system controller 834 enters a defined state appropriate to the test to be performed. Ordinarily, this state will result in the inhibition of both audible alarms and executive actions to prevent causing un-necessary alarm to personnel and the shut-down of plant or equipment.

d) Using the communication link to the transmitter interface 823, the system status monitoring and test unit 835 notifies the transmitter 832 of the amount of target gas that it is to simulate being present in the monitored space 805, along with the duration of the test.

e) Using the known position, width and shape of the target gas absorption line and equations describing the amount of absorption produced by a given quantity of target gas, the notified transmitter 832 drives its laser diode 801 (FIG. 40) with a current waveform including the replica absorption feature(s) necessary to simulate the presence of the notified quantity of target gas in the monitored space.

f) The system status monitoring and test unit 835 collects gas readings from the gas detection system controller 834 corresponding to each gas detection channel that is being tested.

g) The system status monitoring and test unit 835 monitors the alarm status that the gas detection system controller 834 is reporting for each gas detection channel being tested.

h) The system status monitoring and test unit 835 compares the gas readings and alarm status data collected during the test with the readings and behaviour expected for the gas detection system if it is operating correctly.

i) Provided that the test results meet defined criteria, the system status monitoring and test unit 835 notifies the operator and the gas detection system controller 834 that the test has been completed successfully, and the gas detection system returns to its normal, uninhibited state.

j) If the test results do not meet the defined criteria, the system status monitoring and test unit 835 notifies the operator and the gas detection system controller that the test has been failed. In the event of test failure, an operator is expected to perform further tests to confirm the failure, identify its cause and ultimately take steps to remedy the problem.

Despite the relative simplicity of the above test procedure, it achieves very good test coverage, with a successful outcome providing a high degree of confidence in the correct operation of the gas detection system. The very good test coverage is achieved because the gas detection system can only pass the test if for each gas detection channel tested all of the following requirements are met— a) The cables supplying power to the transmitter 832 are in working order and the correct supply voltage and power is reaching the transmitter 832.

b) The microprocessor 819 controlling the operation of the transmitter 832 is operating correctly and is able to receive and understand instructions from the system status monitoring and test unit 835 via the communications link and transmitter interface 823.

c) The transmitter 832 is successfully maintaining the position and width of the target gas absorption line with respect to the wavelength scanning waveform. (The transmitter control software should be written to self-diagnose any failure to maintain the position and width of the target gas absorption line with respect to the wavelength scanning waveform. In the event of diagnosis of a non-correctable failure, the transmitter 832 should stop transmitting or signal a problem.)

d) The laser diode 801 and laser diode drive circuitry 820, 821 are working correctly and the laser diode 801 is producing optical radiation with the required properties.

e) Sufficient optical radiation is getting through the monitored space 805 and reaching the receiver's detector 827 to enable gas detection measurements to be made.

f) The cables supplying power to the receiver 833 are in working order and the correct supply voltage and power is reaching the receiver 33.

g) The microprocessor 830 controlling the operation of the receiver 833 is operating correctly and is able to process the signals from the optical detector 827 to make measurements of the amount of target gas present in the monitored space 805.

h) The receiver output interface 831 is operating correctly and the cables carrying the signal from the receiver output interface 831 to the gas detection system controller 834 are in working order.

i) The input channel of the gas detection system controller 834 corresponding to the gas detector under test is working correctly and is receiving a signal corresponding to a gas reading within the range specified for the test.

j) The gas detection system controller 834 is operating and the alarm status of the channel being tested is being updated correctly, according to the amount of hazardous gas being reported by the gas detector.

Compared to conventional testing of detectors with gas, the test procedure described is very simple and quick, enabling the test to be performed far more regularly and at a much lower cost. The test procedure also lends itself to automatic execution and monitoring, which is not the case with conventional gas testing. For example, testing could be performed once every twenty four hours and would only take the gas detection system off-line for about one minute, a period short enough to have an acceptably small impact upon system availability, especially if one takes account of the large increase in system safety integrity it provides.

In order to ensure high system safety integrity, in the event that the transmitter diagnoses a failure to maintain the position and width of a target gas absorption line with respect to the wavelength scanning waveform that it cannot correct, the transmitter should either stop transmitting or should modulate its laser diode with a signal indicating to the receiver that the transmitter has a problem which requires attention. Subsequently, if the receiver does not receive a signal from the transmitter, or receives a signal from the transmitter indicating that the transmitter has a problem which requires attention, the receiver should change its output to indicate to the gas detection system controller that it has suffered a loss of transmitter signal or has been notified of the presence of a transmitter problem.

Those skilled in the science will appreciate that more than one absorption line of the target gas may scanned by the laser diode 801. In such an arrangement, the retained target gas sample is used to maintain the positions and widths of the two or more absorption lines with respect to the wavelength scanning waveform. When simulating the presence of a quantity of target gas in the monitored space, replica absorption features of the known positions, widths and shapes; and calculated sizes are introduced into the laser diode drive current.

The same principles can also be applied to gas detection or measurement equipment in which two or more laser diodes scan two or more absorption lines of the target gas. In such an arrangement, the retained target gas sample is used to independently maintain the positions and widths of the two or more absorption lines with respect to each laser diode's wavelength scanning waveform. When simulating the presence of a quantity of target gas in the monitored space, replica absorption features of the known positions, widths and shapes; and calculated sizes are introduced into each laser diode's drive current.

Apparatus according to the present invention can also be produced which detects or measures two or more target gases. This can be done either by scanning a single laser diode over separate absorption lines of the different target gases or by scanning two or more laser diodes over the chosen absorption lines of the target gases.

The use of a retained sample of the target gas to provide the transmitter with information upon the position, width and shape of the target gas absorption line with respect to the wavelength scanning waveform is a simple, effective approach. However it is possible to provide the necessary wavelength registration and scaling information to the transmitter without using a retained gas sample, this being especially beneficial if the target gas is unstable or highly reactive and likely to be difficult to retain for any period of time.

The precise position (centre-wavelength), width (linewidth) and shape (broadened Lorentzian) of the target gas absorption line are all known and it is not necessary for the transmitter to be able to accurately measure these properties of the target gas: it is only necessary for the transmitter to accurately know the relationship between drive current and wavelength for its laser diode. Consequently, an optical component with stable, known transmissive or reflective characteristics in the wavelength region of the chosen absorption line can be used to provide a wavelength registration and scaling function. For this, a fraction of the output from the laser diode 801 is directed towards the optical component with known transmissive or reflective characteristics, these characteristics consequently being imprinted onto the illuminating radiation and the signal from the optical detector illuminated by the imprinted radiation processed to provide the necessary wavelength registration and scaling information.

The development of optical components for use in dense wavelength division multiplexed (DWDM) telecommunications systems has resulted in a variety of optical components becoming available with the necessary characteristics and stability, these being key properties required for their use in DWDM systems. Potentially suitable components include fibre-Bragg-grating filters, ultra-narrow-band interference filters and holographic optical elements.

The use by the transmitter of a retained sample of the target gas or an optical component with stable, known transmissive or reflective characteristics to actively maintain the position and width of the target gas absorption line with respect to the wavelength scanning waveform is preferred. However, it is possible to realize many of the functions and features of the claimed invention without actively maintaining the position and width of the target gas absorption line with respect to the wavelength scanning waveform. The means of wavelength registration and scaling is always required but instead of using the information that it provides for active wavelength maintenance, it can be used by the transmitter for the purposes of simulating gas and communicated to the receiver so that the receiver knows where the target gas absorption line is, thus reliably to detect or measure the target gas. This requires a means of communication to be provided between the transmitter and the receiver, and increases the complexity of the signal processing and calculation of the amount of target gas in the monitored space, but is a viable alternative implementation of the claimed invention.

In the high integrity gas detector described with particular reference to FIG. 40, the radiation from the laser diode 801 is collected and transmitted directly through the monitored space 805, subsequently illuminating a receiver detector. However, the claimed invention can also be beneficially employed in an apparatus where a sample of gas from an area to be monitored is drawn into a sample measurement chamber in order to be illuminated and measured using the approaches described.

The apparatus illustrated in FIG. 40 shows the output from the optical detector being amplified, digitized and then processed by a microprocessor. This means of processing the signal from the detector is shown because it is particularly suitable for implementation of the claimed invention. However, it is also possible to realize a high integrity gas detector according to the present invention by means of apparatus wherein the magnitudes and phases of the important frequency components of the detector signal are determined by synchronously detecting them using multiple synchronous detectors operating in parallel at different frequencies upon the same signal. The outputs from the synchronous detectors would subsequently be digitized and used for the calculation of the quantity of target gas present in the monitored space as described.

It is also to be understood that the means of splitting, collection and collimation of the optical radiation from the laser diode 801 need not be limited to the simple optical elements shown in FIG. 40. The optical elements used for this purpose can alternatively comprise a number of separate optical elements combined to perform the required functions of laser diode radiation splitting, collection, collimation and transmission through the monitored space. Furthermore, these optical elements need not be limited to the free-space optical elements shown. The radiation from the laser diode can be coupled into fibre-optic cable and carried to one or more optical elements that will collimate and transmit the radiation through the monitored space.

The reading of the gas detector of FIG. 40 can be output in various ways including: an analogue electrical output, producing a voltage or current signal proportional to the quantity of target gas; a digital output producing an electronic signal conforming to a defined protocol and containing numerical data conveying the concentration or quantity of gas; the opening or closing of relays at prescribed gas concentrations; and an analogue or digital display.

Target Gas Fingerprinting

Figure 42:
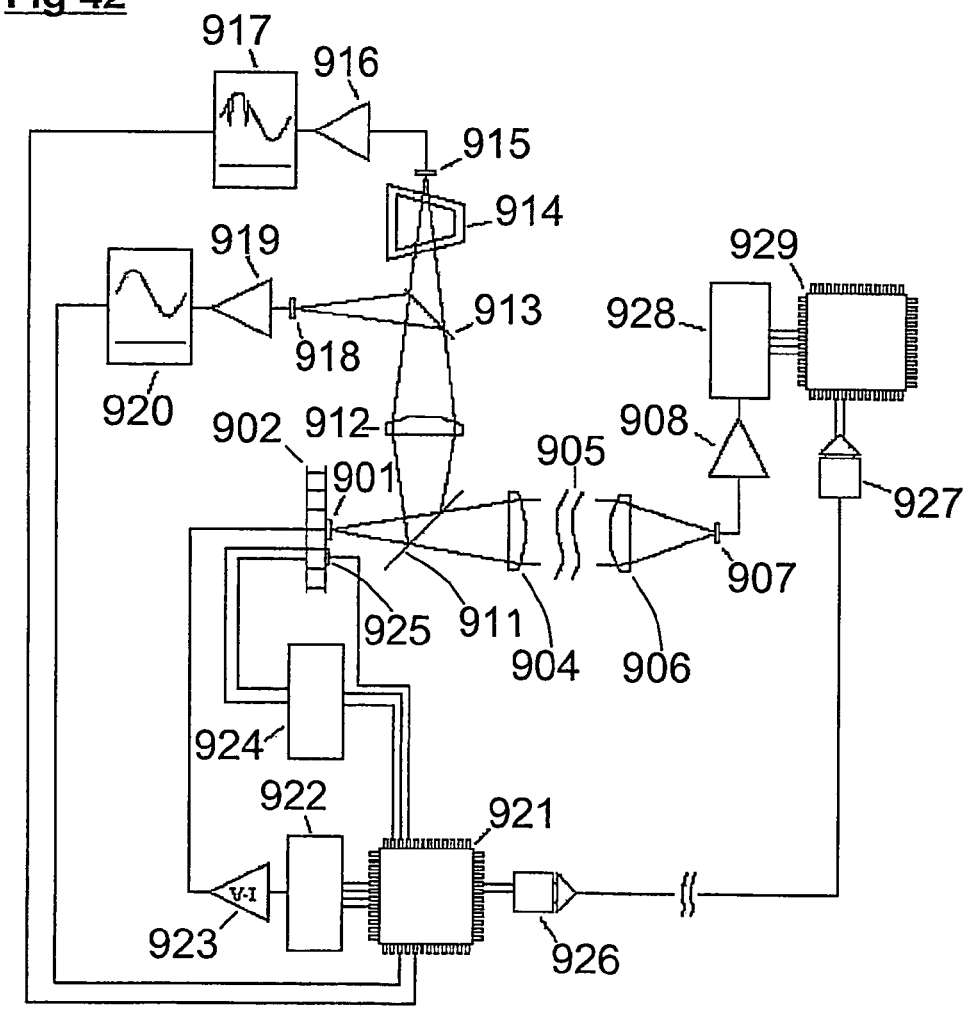
FIG. 42 shows gas fingerprinting apparatus according to the present invention.

Referring to FIG. 42, a laser diode 901 is mounted on a temperature controlled mount 902. Optical radiation emitted by the laser diode 901 is sampled by a beam-sampler 911. The majority of the radiation passing beam-sampler 911 is collimated by an optical element 904, transmitted through a monitored space 905 and collected and concentrated onto a first optical detector 907 by a receiver optical element 906. The sampled laser diode radiation is concentrated by an optical element 912 and split into two fractions by a beam-splitter 913. One fraction of this split sample passes through a retained target gas sample 914 before being detected by a second optical detector 915, and the other fraction is detected by a third optical detector 918. The signals from the optical detectors 915 and 918 are respectively amplified by amplifier chains 916 and 919, and digitized by ADCs 917 and 920 respectively, the digitized waveforms being then passed to a microcontroller 921. The digitized waveform from the second optical detector 915 contains information regarding the effect of absorption of laser diode radiation by the retained target gas sample 914; whilst that for the third optical detector 918 contains information regarding the output of laser diode 901 in the absence of target gas absorption.

The microcontroller 921 controls the synthesis of a laser diode drive current waveform, and provides a DAC 922 with a sequence of digital values to convert into an analogue voltage waveform, this waveform subsequently being converted into a current by a V-I converter 923. The laser diode control current waveform comprises two components, a bias component that effectively defines the mean wavelength at which the laser diode 901 operates and a sinusoidal wavelength scanning component that cyclically scans the laser diode's wavelength. The microcontroller 921 also controls the temperature of the laser diode 901, by adjusting the current that is output by temperature controlled mount driver 924, with feedback of the temperature of the mount 902 being provided by a temperature sensing element 925.

The microcontroller 921 processes the digitized waveforms from the optical detectors 915 and 918 to determine the magnitudes and phases of the fundamental and harmonic components of the wavelength scanning frequency present in these waveforms. This information is used by the microcontroller 921 to control the precise operating conditions of the laser diode 901, such that absorption of laser diode radiation by target gas produces a distortion 'fingerprint' of the gas with very specific characteristics. Information regarding the target gas distortion fingerprint and the optical output of the laser diode 901 with no target gas absorption is communicated to the receiver via digital communication interfaces 926 and 927.

The signal from the receiver optical detector 907 is amplified by the amplifier chain 908 and digitized by an ADC 28, the resulting digitized waveform being passed to a receiver microcontroller 929. The receiver microcontroller 929 processes the received waveform to determine the magnitudes and phases of the fundamental and harmonic components of the wavelength scanning frequency present in this waveform. The receiver microcontroller 929 normalizes the received waveform and then subtracts the harmonic components known to be present in the optical output of the laser diode with no target gas absorption, so that any residual harmonic components are either due to absorption by target gas in the monitored space, or are the result of system noise, absorption by atmospheric gases or coherence/fringe effects. The residual harmonics are compared to the fingerprint known to be produced by target gas absorption and provided that the magnitudes and phases of the harmonics exhibit a good correlation with the fingerprint, the magnitudes of the harmonics are used to calculate the amount of target gas present in the monitored space. If the residual harmonics do not exhibit a good correlation with the target gas fingerprint it is most likely that they are the result of system noise, absorption by interfering atmospheric gases or coherence/fringe effects and such data is rejected.

In order for the fingerprint of target gas absorption to be reliably distinguished from system noise, absorption by atmospheric gases and coherence/fringe effects, it is necessary to create a harmonic fingerprint with very specific characteristics. Controlling the operating and drive conditions of the laser diode so that absorption of its radiation by target gas produces a very specific harmonic fingerprint is an important feature of the present invention.

Figure 43:
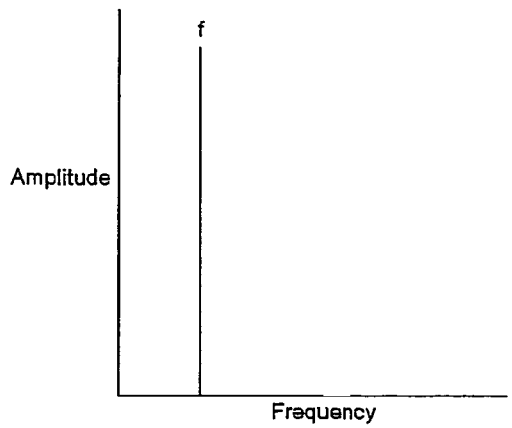
FIG. 43 shows the Fourier transform of a perfect detector output waveform with no target gas absorption.

FIG. 43 shows the Fourier transform of a perfect detector output waveform with no target gas absorption, with just a single frequency component at the fundamental frequency of the wavelength scanning component.

Figure 44:
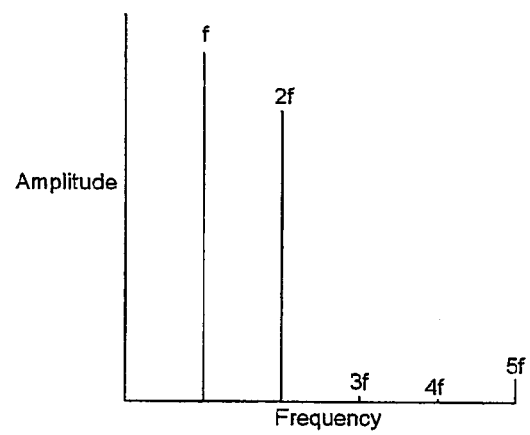
FIG. 44 shows the typical Fourier transform of a detector output waveform with strong target gas absorption.

FIG. 44 shows the typical Fourier transform of a detector output waveform with strong target gas absorption, with significant fundamental and second harmonic components and a number of small amplitude, higher harmonics. The harmonic fingerprint in FIG. 43 is typical of that generated by conventional LDS equipment but does not contain sufficiently specific characteristics to enable it to be reliably distinguished from system noise, absorption by atmospheric gases or coherence/fringe effects. The fundamental component is always present in the detected signal and the presence of only one harmonic of significant amplitude means that it is only necessary for noise, absorption by atmospheric gases or coherence/fringe effects to produce a component at this frequency in order to appear to indicate the presence of target gas absorption. The probability of such events occurring is too high for the use of conventional LDS equipment in safety related applications.

Figure 45:
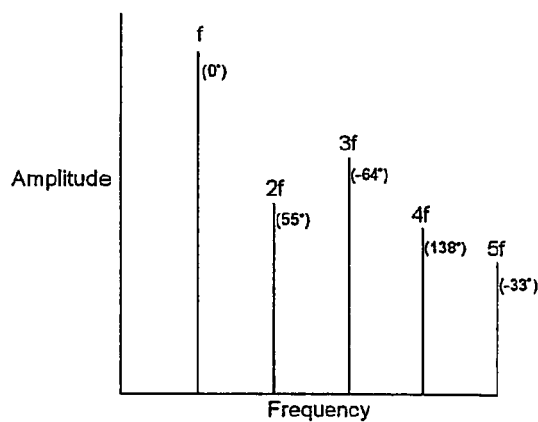
FIG. 45 shows an example of the complex Fourier transform of a target gas absorption 'fingerprint' with the specific characteristics necessary for successful implementation of the claimed invention.

FIG. 45 shows an example of the complex Fourier transform of a target gas absorption fingerprint with the specific characteristics necessary for successful implementation of the claimed invention. (For ease of presentation, the magnitude of each frequency component is represented by the height of the corresponding line; whilst the phase angle of each component with respect to the fundamental is written in brackets to the right of each line.) There are a number of characteristics of this target gas absorption fingerprint which make it possible to reliably distinguish it from system noise, absorption by atmospheric gases or coherence/fringe effects. The target gas absorption fingerprint includes the following distinguishing features— a) The presence of two or more harmonics of the wavelength scanning frequency with substantial magnitudes;

b) The presence of two or more harmonics of the wavelength scanning frequency with known relative magnitudes; and c) The presence of two or more harmonics of the wavelength scanning frequency, with known, fixed phases with respect to the fundamental.

The requirement that there be two or more harmonics of the wavelength scanning frequency with substantial magnitudes assists with distinguishing genuine target gas absorption because it becomes necessary for any potentially interfering effect or event to simultaneously have a significant effect at two or more frequencies. The probability of potentially interfering effects simultaneously having a significant effect at two or more frequencies is considerably lower than the probability of significant interference at a single frequency.

The requirement that there be two or more harmonics of the wavelength scanning frequency with known relative magnitudes assists with distinguishing genuine target gas absorption because it requires any potentially interfering effect or event to generate harmonics with the same relative magnitudes as target gas absorption. The probability of a potentially interfering effect or event simultaneously producing two or more harmonics with prescribed relative magnitudes is considerably lower than the probability of interfering effects simultaneously producing two or more harmonics of un-prescribed relative magnitudes.

The requirement that there be two or more harmonics of the wavelength scanning frequency, with known, fixed phases with respect to the fundamental assists with distinguishing genuine target gas absorption because it requires any potentially interfering effect or event to generate harmonics with known, prescribed phases. The probability of a potentially interfering effect or event simultaneously producing two or more harmonics with prescribed phases is considerably lower than the probability of interfering effects simultaneously producing two or more harmonics of un-prescribed phases.

The combined effect of requiring any potentially interfering effect or event to simultaneously meet all of the requirements of the target gas fingerprint is such as to greatly reduce the probability of interfering effects or events giving rise to false alarms or spurious readings compared to conventional LDS techniques.

At this point it is worth considering in more detail how the target gas absorption fingerprint requirements enable different types of potentially interfering effects or events to be reliably distinguished from genuine target gas absorption.

In a system with reasonable signal-to-noise ratio (essential for any sensitive LDS technique) there is a small but significant probability of system noise generating a single harmonic frequency of a level sufficient to generate a false alarm or spurious reading. However, the probability of system noise simultaneously generating two or more harmonic frequencies with prescribed relative magnitudes is extremely low, without taking the phase prescription into consideration. Consequently, the multiple frequency and relative magnitude requirements of the fingerprint would be sufficient to deal with system noise effects, without having to call upon the phase discriminator.

Figure 46:
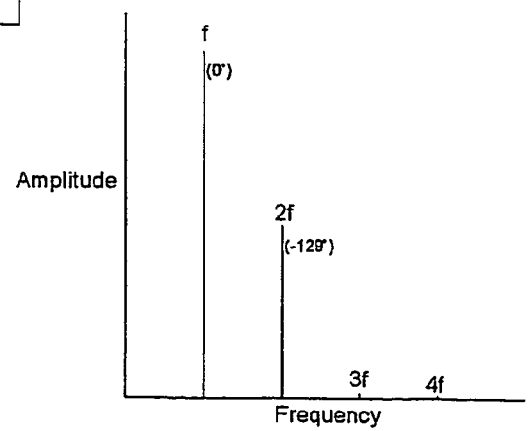
FIG. 46 shows the typical Fourier transform produced as a result of scanning a target gas absorption region close to a strong atmospheric absorption line, with no target gas present.

In a system operating with an open path through the atmosphere it is usually possible to find one or more target gas absorption lines which do not coincide with absorption lines of atmospheric gases. The worst-case scenario tends to be the presence of strong atmospheric absorption lines at wavelengths near to the target gas absorption line, but not coinciding. These nearby atmospheric lines cause problems to conventional LDS systems because they can generate significant harmonics of the wavelength scanning frequency. FIG. 45 shows the typical Fourier transform produced as a result of scanning a target gas absorption region close to a strong atmospheric absorption line, with no target gas present. Those skilled in the science will note the significant second harmonic component generated by the presence of the nearby strong atmospheric absorption line but the small third and fourth harmonics. Provided that the target gas absorption line is being scanned over a region that does not contain the maxima of the strong atmospheric absorption line, the harmonic pattern of FIG. 46 is produced, with the third and fourth harmonics always very much smaller than the second harmonic. Consequently, the relative magnitude requirements of the 'fingerprint' will in most instances be sufficient to deal with nearby atmospheric absorption lines, without having to call upon the phase discriminator.

Even in an LDS system carefully designed to minimise coherence/fringe effects, such effects will generate harmonics of the wavelength scanning frequency with magnitudes sufficient to cause problems when attempting to detect fractional absorbances of the order of $1 \times 10^{-4}$ to $1 \times 10^{-5}$. Furthermore, owing to the nature of coherence/fringe effects, these harmonics will tend to vary slowly with temperature and time, with the potential to simultaneously generate two or more harmonics with significant magnitudes. In order to deal successfully with harmonics generated by coherence/fringe effects, it is necessary to make use of the full suite of target gas 'fingerprint' characteristics of the claimed invention. This is because; whilst the probability of coherence/fringe effects generating two or more harmonics with prescribed relative magnitudes is low, it is not low enough to be ignored. Requiring coherence/fringe effects to meet both prescribed relative magnitude and phase requirements is necessary to push down the probability of false alarms and spurious readings to a level acceptable for safety related applications.

Those skilled in the science will appreciate from the foregoing paragraph that coherence/fringe effects are more problematic than other potentially interfering effects or events. Indeed, in general coherence/fringe effects tend to set the limits of detection for most equipment employing LDS techniques.

The ability of the present invention to distinguish genuine target gas absorption from coherence/fringe effects by the fingerprint technique is enhanced by the use of an optical detector 918 (FIG. 42) to measure the output from the laser diode 901 in the absence of target gas absorption. This is because the largest and most problematical coherence/fringe effects are associated with the laser diode and its package and window. By continuously measuring the output of the laser diode 901 and communicating this information to the receiver, any variations in the harmonic content output by the laser diode 901 arising from coherence/fringe effects can be subtracted when the receiver processes the waveform that it is receiving. Since these are the largest and most problematical coherence/fringe effects, their subtraction contributes significantly to lessening the impact of coherence/fringe effects.

In the fingerprinting apparatus of FIG. 42, the laser diode radiation is collected and transmitted through the monitored space, subsequently illuminating a receiver detector. However, the invention can also be beneficially employed in an apparatus where a sample of gas to be measured is drawn into a sample measurement chamber in order to be illuminated and measured using the approaches described. This arrangement might be of particular use in applications such as process control, or where it is not practicable to transmit a measurement beam through the gas without some prior sample conditioning.

Various possible modifications may be made to the apparatus hereinbefore described without departing from the present invention. For instance, the means of collection and collimation of the optical radiation from the laser diode(s) need not be limited to the simple optical elements shown in the drawings. The optical elements used for this purpose can instead comprise a number of separate optical elements combined to perform the required function of laser diode radiation collection, collimation and transmission through the monitored space. Furthermore, these optical elements need not be limited to the free-space optical elements shown. The radiation from the laser diode(s) can be coupled into fibre-optic cable(s) and carried to one or more optical elements arranged to collimate and transmit the radiation through the monitored space.

Readings or measurements from apparatus according to the present invention may be output by various means, depending principally upon how and by what the readings or measurements are to be used. The means of output for readings or measurements could for instance include an analogue electrical signal proportional to the concentration or quantity of gas, a digital electronic signal conforming to a defined protocol and containing numerical data conveying the concentration or quantity of gas, a numerical representation of the concentration or quantity of gas upon a display and the opening or closing of relays at prescribed concentrations or quantities of gas.

As will be noted, it is possible to tune the laser(s) to define two wavelengths $\Lambda_1$ and $\Lambda_2$ which are respectively close to two separate optical absorption lines of the target gas. This feature enables additional techniques and benefits as noted above, including notably the ability to 'fingerprint' target gases. Those skilled in the art will appreciate that, while laser diodes are readily available and conveniently tuned by means of a control current, laser diodes may also be controlled by other means such as voltage control, lasers other than laser diodes may be tuned in quite different ways and tunable devices other than laser diodes may be of use. Accordingly, whereas current-controlled laser diodes have been specifically referred to in the foregoing description, other narrow bandwidth optical sources which can be accurately tuned to two separate wavelengths may be used, and the term 'laser diode' should herein be construed accordingly.

Other modifications and adaptations will be apparent to those skilled in the science.

What is claimed is:

1. A method of detecting a target gas in a monitored space comprising applying an electrical control current to a laser diode so as to generate optical radiation of a wavelength defined by the control current, transmitting the optical radiation across the monitored space and determining the optical absorption thereof, wherein:

the control current defines two mean wavelengths $\Lambda_1$ and $\Lambda_2$ for the optical radiation and includes electrical modulation at two frequencies f and f' respectively; and wherein $\Lambda_1$ and $\Lambda_2$ are respectively close to two separate optical absorption lines of the target gas and f and f' are not harmonically related.

2. A method of detecting a target gas in a monitored space as claimed in claim 1 wherein the optical radiation is generated from a single laser diode and the control current comprises a bias component which is alternated between two values respectively defining $\Lambda_1$ and $\Lambda_2$.

3. A method of detecting a target gas in a monitored space as claimed in claim 1 wherein the optical radiation is generated from two laser diodes of which one has a said control current comprising a bias component of value defining $\Lambda_1$ and the other has a said control current comprising a bias component defining $\Lambda_2$.

4. A method of detecting a target gas in a monitored space as claimed in claim 2 wherein the electrical modulation is sinusoidal.

5. A method of detecting a target gas in a monitored space as claimed in claim 3 wherein the electrical modulation is sinusoidal.

6. Apparatus for detecting a target gas in a monitored space, which apparatus comprises a laser diode operable to transmit radiation across the monitored space and a first optical receiver operable to receive the transmitted radiation and determine optical absorption thereof, wherein:

a control current is applied to the laser diode to define two mean wavelengths $\Lambda_1$ and $\Lambda_2$ for the optical radiation and is electrically modulated at two frequencies f and f' respectively; and $\Lambda_1$ and $\Lambda_2$ are respectively close to two separate optical absorption lines of the target gas and f and f' are not harmonically related.

7. Apparatus for detecting a target gas in a monitored space as claimed in claim 6 wherein the apparatus comprises a single laser diode and the control current applied thereto comprises a bias component alternated between two values respectively defining $\Lambda_1$ and $\Lambda_2$.

8. Apparatus for detecting a target gas in a monitored space as claimed in claim 7, which apparatus is arranged for the detection of methane, ethane, propane or ethylene, wherein:

the bias component of the laser diode control current is varied in a manner determined to operate the laser diode at wavelengths suitable for scanning either of methane's absorption lines at 1684 nm and 1687.3 nm and one or more of the other gases' absorption lines or features at 1684.3 nm, 1686.4 nm and 1687.0 nm;

the scanning component repetitively scans the laser diode's wavelength over the chosen absorption lines or features;

the optical radiation from the laser diode is collected and transmitted through the monitored space and subsequently illuminates an optical detector; and an electrical signal from this optical detector is processed to determine the gas or gases present in the monitored space and the amounts of each gas present.

9. Apparatus for detecting a target gas in a monitored space as claimed in claim 8 wherein the amount of methane gas present in the monitored space is determined and then the amount of hydrogen sulphide present is estimated using a coefficient relating the amount of methane to the amount of hydrogen sulphide for the solution gas of a particular field or facility.

10. Apparatus for detecting a target gas in a monitored space as claimed in claim 9 wherein said apparatus includes means to update said coefficient.

11. Apparatus for detecting a target gas in a monitored space as claimed in claim 9, which apparatus is arranged to deliver outputs representing the concentrations or quantities of gases calculated or estimated present in the monitored space or sample measurement chamber, wherein said outputs include:

analogue electrical signals proportional to the concentration or quantity of each gas;

a digital electronic signal conforming to a defined protocol and containing numerical information conveying the concentration or quantity of each gas; and a numerical representation of the concentration or quantity of each gas.

12. Apparatus for detecting a target gas in a monitored space as claimed in claim 9 wherein said apparatus comprises two laser diodes, one operated at wavelengths to scan absorption lines of flammable gases including methane, ethane and propane, the other operated at a wavelength to scan an absorption line of hydrogen sulphide.

13. Apparatus for detecting a target gas in a monitored space as claimed in claim 12 comprising an alarm actuated when hazardous gases are detected by the apparatus, wherein the alarm is actuated only when the apparatus detects both hydrogen sulphide and methane.

14. Apparatus for detecting a target gas in a monitored space as claimed in claim 13 wherein the alarm is actuated only when the detection apparatus detects methane above a predetermined threshold level.

15. Apparatus for detecting a target gas in a monitored space as claimed in claim 14 wherein said threshold level is determined from records of the sourness of petrochemicals handled at the facility.

16. Apparatus for detecting a target gas in a monitored space as claimed in claim 7, which apparatus is arranged for the detection of hydrogen sulphide, wherein:

the bias component of the laser diode control current is varied in a manner determined to operate the laser diode at one or more wavelengths suitable for scanning any of methane's optical absorption lines or features;

the scanning component repetitively scans the laser diodes wavelength over the chosen absorption line(s) or feature(s);

the optical radiation from the laser diode is collected and transmitted through the monitored space and subsequently illuminates an optical detector; and an electrical signal from this optical detector is processed to determine the amount of methane gas present in the monitored space;

whereafter the amount of hydrogen sulphide present is estimated using a coefficient relating the amount of methane to the amount of hydrogen suiphide for the solution gas of a particular field or facility.

17. Apparatus for detecting a target gas in a monitored space as claimed in claim 16 wherein said apparatus includes means to update said coefficient.

18. Apparatus for detecting a target gas in a monitored space as claimed in claim 16, which apparatus is arranged to deliver outputs representing the concentrations or quantities of gases calculated or estimated present in the monitored space or sample measurement chamber, wherein said outputs include:

analogue electrical signals proportional to the concentration or quantity of each gas;

a digital electronic signal conforming to a defined protocol and containing numerical information conveying the concentration or quantity of each gas; and a numerical representation of the concentration or quantity of each gas.

19. Apparatus for detecting a target gas in a monitored space as claimed in claim 16 wherein said apparatus comprises two laser diodes, one operated at wavelengths to scan absorption lines of flammable gases including methane, ethane and propane, the other operated at a wavelength to scan an absorption line of hydrogen sulphide.

20. Apparatus for detecting a target gas in a monitored space as claimed in claim 19 comprising an alarm actuated when hazardous gases are detected by the apparatus, wherein the alarm is actuated only when the apparatus detects both hydrogen sulphide and methane.

21. Apparatus for detecting a target gas in a monitored space as claimed in claim 19 wherein the alarm is actuated only when the detection apparatus detects methane above a predetermined threshold level.

22. Apparatus for detecting a target gas in a monitored space as claimed in claim 21 wherein said threshold level is determined from records of the sourness of petrochemicals handled at the facility.

23. Apparatus for detecting a target gas in a monitored space as claimed in claim 7 wherein:

the optical radiation from the laser diode is split into two fractions;

one said fraction is passed through a retained sample of the target gas and illuminates an optical detector, the signal from this optical detector being used by the transmitter to maintain the position and width of the target gas absorption line with respect to the scanning component waveform;

the second said fraction is transmitted through a monitored space to illuminate an optical detector in a receiver, the signal from this optical detector being processed to calculate the quantity of target gas present in the monitored space, this quantity being output by the receiver; and wherein the transmitter includes means of electronically introducing a replica absorption feature into the intensity of the optical output of the laser diode, the position, width and shape of the replicated absorption feature corresponding to that known to be produced by the absorption line of the target gas and being actively maintained by the transmitter, and the size of the replicated absorption feature being a controlled variable, calculated to simulate the presence of a nominated quantity of target gas in the monitored space.

24. Apparatus for detecting a target gas in a monitored space as claimed in claim 23 wherein:

the drive current to the laser diode is produced by a digital synthesizer which uses a Digital-to-Analogue Converter (DAC) to output a sequence of voltages which are turned into a current by a voltage to current (V-I) converter;

the sequence of voltages is calculated to produce the desired current waveforms, the waveforms including those necessary to bias and scan the laser diode; and when required a replica absorption feature is introduced into the output of the laser diode simulating the presence of a nominated quantity of target gas in the monitored space.

25. Apparatus for detecting a target gas in a monitored space as claimed in claim 23 wherein:

the laser diode in the transmitter scans a total of two or more chosen absorption lines of one or more target gases;

the retained gas sample includes a quantity of each of the one or more target gases and is used to maintain the position and width of each chosen absorption line of the one or more target gases with respect to the scanning component waveform;

the transmitter includes means of electronically introducing replica absorption features into the intensity of the optical output of the laser diode; and wherein the position, width and shape of these replica absorption features correspond to that known to be produced by the one or more target gases' absorption lines and being actively maintained by the transmitter, and the sizes of the replica absorption features are controlled variables, calculated to simulate the presence of nominated quantities of the one or more target gases in the monitored space.

26. Apparatus for detecting a target gas in a monitored space as claimed in claim 23 wherein said apparatus comprises two or more laser diodes arranged to detect or measure one or more target gases and wherein:

the output from each laser diode is split into two fractions, one fraction used to illuminate a retained sample of the one or more target gases to maintain the position and width of the one or more absorption lines with respect to the scanning component waveform, and the other fraction transmitted through a monitored space to a receiver;

the receiver is capable of detecting and processing the optical signals from the two or more laser diodes to calculate the quantities of the one or more target gases in the monitored space;

the transmitter is provided with means of electronically introducing replica absorption features into the intensity of the optical output of each of the laser diodes, the position, width and shape of the replicated absorption features corresponding to that known to be produced by the target gases' absorption lines and being actively maintained by the transmitter, and the sizes of the replicated absorption features being controlled variables, calculated to simulate the presence of nominated quantities of the one or more gases in the monitored space.

27. Apparatus for detecting a target gas in a monitored space as claimed in claim 23 wherein means are provided for an operator or control system to instruct the transmitter to simulate the presence of nominated quantities of one or more target gases in the monitored space, the transmitter subsequently electronically simulating the presence of the nominated quantities of the one or more target gases.

28. Apparatus for detecting a target gas in a monitored space as claimed in claim 23 wherein in the event that the transmitter diagnoses a failure to maintain the position and width of the one or more target gas absorption lines with respect to the scanning component waveform that it cannot correct, the transmitter either stops transmitting or modulates its laser diode with a signal indicating to the receiver that the transmitter has a problem which requires attention.

29. Apparatus for detecting a target gas in a monitored space as claimed in claim 28 wherein, in the event that the receiver does not receive a signal from the transmitter, or receives a signal from the transmitter indicating that the transmitter has a problem which requires attention, the receiver changes its output to indicate the loss of transmitter signal or the presence of a transmitter problem.

30. Apparatus for detecting a target gas in a monitored space as claimed in claim 23 wherein the transmitter and the receiver are physically part of a single gas detection or measurement apparatus, and wherein gas is drawn or diffuses into a sample measurement chamber in order to be illuminated by laser diode radiation and measured.

31. Apparatus for detecting a target gas in a monitored space as claimed in claim 23 wherein instead of illuminating a retained sample of the target gas for wavelength registration purposes, a fraction of the output from the transmitter's laser diode illuminates an optical component possessing transmissive or reflective properties determined to provide the wavelength registration function, having illuminated said component, the transmitted or reflected illumination being concentrated onto an optical detector in the transmitter.

32. Apparatus for detecting a target gas in a monitored space as claimed in claim 31 wherein said optical component includes a narrow-band interference filter, a diffraction grating, a holographic optical element, an etalon or a fiber Bragg-grating.

33. Apparatus for detecting a target gas in a monitored space as claimed in claim 23 wherein:
the position and width of the target gas absorption line with respect to the scanning component waveform is not actively maintained by the transmitter, the signal from the optical detector in the transmitter instead being used solely to monitor the position, width and shape of the target gas absorption line with respect to the scanning component waveform;
means of communication is provided between the transmitter and the receiver, such means being used to provide the receiver with data relaying the position, width and shape of the target gas absorption line;
a signal from the receiver's detector is processed using the available target gas absorption line position, width and shape data to calculate the quantity of target gas present in the monitored space, this quantity being output by the receiver;
the transmitter includes means of electronically introducing a replica absorption feature into the intensity of the optical output of the laser diode, the position, width and shape of the replicated absorption feature corresponding to that known to be produced by the target gas' absorption line, and the size of the replicated absorption feature being a controlled variable, calculated to simulate the presence of a nominated quantity of target gas in the monitored space.

34. Apparatus for detecting a target gas in a monitored space as claimed in claim 23 wherein the means of collecting the laser diode radiation and transmitting it through the monitored space includes combinations of free-space optical elements and/or fiber-optics.

35. Apparatus for detecting a target gas in a monitored space as claimed in claim 6 wherein the apparatus comprises two laser diodes of which one has a control current comprising a bias component defining $\Lambda_1$ and the other has a control current comprising a bias component defining $\Lambda_2$.

36. Apparatus for detecting a target gas in a monitored space as claimed in claim 35 wherein the electrical modulation applied to each laser diode is sinusoidal.

37. Apparatus for detecting a target gas in a monitored space as claimed in claim 36 wherein:
said sinusoidal component is synchronously alternated between the two non-harmonically related electrical frequencies f and f' at which the laser's wavelength is scanned across one or the other of the chosen absorption lines for a prescribed interval;
the optical radiation from the laser diode is collected and transmitted through the monitored space and subsequently illuminates an optical detector; and
an electrical signal from this optical detector is amplified, digitized and processed to determine the magnitudes of frequency components f, f', $f_1$ and $f_2$, where frequencies $f_1$ and $f_2$ are similar order harmonics of the non-harmonically related electrical frequencies f and f', normalization of the magnitudes of $f_1$ and $f_2$ with respect to their fundamentals.

38. Apparatus for detecting a target gas in a monitored space as claimed in claim 37 wherein said apparatus includes means operative:
to calculate quantities $Q_1$ and $Q_2$, separate estimates of the amount of target gas in the monitored space based upon the normalized magnitude of frequency components $f_1$ and $f_2$;
to compare quantities $Q_1$ and $Q_2$, to determine the quality of their agreement with each other and previous results for measurements made through the monitored space; and
to apply rules dependent upon this quality, and use $Q_1$ and $Q_2$ in combination with previous results to calculate the quantity of target gas present in the monitored space.

39. Apparatus for detecting a target gas in a monitored space as claimed in claim 37 wherein the wavelength scanning ranges for each laser diode are non-harmonically related and have significantly different characteristic distances with respect to the formation of coherent interference fringes.

40. Apparatus for detecting a target gas in a monitored space as claimed in claim 37 wherein:
each target gas absorption line is scanned at two, non-harmonically related electrical frequencies and measurements of any absorption by such lines are made by determining the magnitude of the two, similar order harmonics of the non-harmonically related scanning frequencies; and wherein
this process is carried out for each absorption line being scanned;
and wherein this process is performed simultaneously, all electrical scanning frequencies being chosen to be non-harmonically related.

41. Apparatus for detecting a target gas in a monitored space as claimed in claim 37 wherein that the two mean wavelengths close to two separate optical absorption lines of the same target gas are chosen such that:
(a) both are in regions of low absorption by atmospheric gases; or
(b) one is in a region of low absorption by atmospheric gases while the other is in a region of higher absorption by atmospheric gases; or
(c) one is in a region affected by absorption by one particular atmospheric gas species while the other is in a region affected by absorption by another atmospheric gas species.

42. Apparatus for detecting a target gas in a monitored space as claimed in claim 37 wherein the rules governing the use of two estimated gas quantities $Q_1$ and $Q_2$ in combination with results for previous measurements made through the monitored space to calculate the quantity of gas present in the monitored space are such that:
(a) if $Q_1$ and $Q_2$ are in close agreement, a large fraction of the average of $Q_1$ and $Q_2$ is added to a balancing fraction of the running average of previous results; while (b) if $Q_1$ and $Q_2$ are in reasonable but not close agreement, a lesser fraction of the average of $Q_1$ and $Q_2$ is added to a larger balancing fraction of the running average of previous results; while (c) if only $Q_1$ or only $Q_2$ is in close or reasonable agreement with the running average of previous results, the quantity which is not in close or reasonable agreement is rejected while a lesser fraction of the close or reasonably agreeing quantity is added to a larger balancing fraction of the running average of previous results; while (d) if $Q_1$ and $Q_2$ are in poor agreement with each other and the running average of previous results, both $Q_1$ and $Q_2$ are rejected and only the running average of previous results is used.

43. Apparatus for detecting a target gas in a monitored space as claimed in claim 37 wherein the results of measurements performed upon target gas lines in regions of known low absorption by atmospheric gases are used to discriminate the effects of absorption by atmospheric gases in regions of more significant absorption by atmospheric gases from genuine changes in target gas concentration, thereby enabling any offsets arising from such absorption to be compensated for.

44. Apparatus for detecting a target gas in a monitored space as claimed in claim 37 wherein the diode lasers are VCSELs.

45. Apparatus for detecting a target gas in a monitored space as claimed in claim 37 wherein the means of collecting the laser radiation and transmitting it through the monitored space includes combinations of free-space optical elements and fiber-optics.

46. Apparatus for detecting a target gas in a monitored space as claimed in claim 37 wherein instead of amplifying, digitizing and digitally processing the detector signal(s) to determine the magnitudes of the various frequency components, the frequency component magnitudes are determined by amplifying the detector signal(s) and synchronously detecting the various frequency components using multiple synchronous detectors operating in parallel upon the signal(s).

47. Apparatus for detecting a target gas in a monitored space as claimed in claim 37 wherein said gas is drawn into a sample measurement chamber in which it is illuminated by the laser diode radiation.

48. Apparatus for detecting a target gas in a monitored space as claimed in claim 37 wherein said apparatus is arranged to detect hydrogen sulphide by measurement of any combination of two or more of the hydrogen sulphide absorption lines at 1582.13 nm, 1589.24 nm, 1589.42 nm, 1589.54 nm, 1589.97 nm and 1593.05 nm.

49. Apparatus for detecting a target gas in a monitored space as claimed in claim 37 wherein the means of output for the concentration or quantity of gas calculated present in the monitored path or sample measurement chamber includes:

an analogue electrical signal proportional to the concentration or quantity of gas;

a digital electronic signal conforming to a defined protocol and containing numerical information conveying the concentration or quantity of gas; and a numerical representation of the concentration or quantity of gas upon a display which is associated with or forms part of the apparatus, or the opening or closing of relays at prescribed concentrations or quantities of gas, such relays and the necessary control circuitry either being associated with or forming part of the apparatus.

50. Apparatus for detecting a target gas in a monitored space as claimed in claim 6 wherein:

said apparatus includes an optical splitter operative to split the radiation into two fractions of which one fraction is transmitted across the monitored space to said first optical receiver and the other is passed through a retained sample of the target gas to a second optical receiver;

the control current applied to the laser diode is controlled by a feedback signal from said second optical receiver so that absorption of the radiation has a distortion pattern specific to the target gas, characterized in that said distortion pattern includes two harmonics of the modulation frequency, each of substantial magnitude.

51. Apparatus for detecting a target gas in a monitored space as claimed in claim 50 wherein the distortion pattern includes an even harmonic and an odd harmonic.

52. Apparatus for detecting a target gas in a monitored space as claimed in claim 50 wherein the distortion pattern includes three harmonics of substantial magnitude.

53. Apparatus for detecting a target gas in a monitored space as claimed in claim 50 wherein said harmonics have a predetermined relationship in both magnitude and phase angle.

54. Apparatus for detecting a target gas in a monitored space as claimed in claim 53 wherein the quantity of target gas present in the monitored space is calculated from the signal from the first optical receiver and the specific distortion pattern.

55. Apparatus for detecting a target gas in a monitored space as claimed in claim 50 wherein the transmitter includes an optical detector to which a further fraction of the optical radiation is directed by the optical splitter, and said detector produces a signal representing the magnitude and phase of any component of said distortion pattern present in the radiation from the laser diode in the absence of absorption by target gas and said signal is subtracted from the output of the first optical receiver.

56. Apparatus for detecting a target gas in a monitored space as claimed in claim 50 wherein the control current is produced by a digital synthesizer including a digital-to-analogue converter (DAC) to output a sequence of voltages and a voltage-to-current (V-I) converter to convert said voltages into a current.

57. Apparatus for detecting a target gas in a monitored space as claimed in claim 50 wherein the laser diode sequentially scans a plurality of selected absorption lines of a target gas.

58. Apparatus for detecting a target gas in a monitored space as claimed in claim 57, which apparatus is operable to scan selected absorption lines of a plurality of target gases, wherein said retained sample includes a quantity of each said gas.

59. Apparatus for detecting a target gas in a monitored space as claimed in claim 57 wherein said apparatus comprises a plurality of said optical transmitters and one said optical receiver operative to receive transmitted radiation from each of said plurality.

60. Apparatus for detecting a target gas in a monitored space as claimed in claim 50 wherein the apparatus includes measurement means operative to calculate the quantity of target gas in the monitored space.

61. Apparatus for detecting a target gas in a monitored space as claimed in claim 60 wherein the monitored space is defined by a measurement chamber into which in use the target gas is admitted and illuminated by said radiation.

62. Apparatus for detecting a target gas in a monitored space as claimed in claim 60 wherein the measurement means provides an output indicating the calculated quantity of target gas, and said output comprises an analogue representation of said quantity, a digital representation of said quantity and a numerical display of said quantity signal.

63. Apparatus for detecting a target gas in a monitored space as claimed in claim 62 wherein the apparatus includes an alarm operative automatically to signal measurement of a quantity of gas above a predetermined threshold.

64. Apparatus for detecting a target gas in a monitored space as claimed in claim 50 including means to collect the optical radiation and transmit it across the monitored space, wherein said means includes combinations of free-space optical elements and/or fiber-optics.

65. Apparatus for detecting a target gas in a monitored space as claimed in claim 6 wherein:
   the laser diode control current has bias and wavelength scanning components so arranged that absorption of optical radiation from the laser diode by target gas produces a specific distortion 'fingerprint' including at least two harmonics of the wavelength scanning component frequency each of substantial magnitude and known, fixed magnitude ratio(s) and phase angles;
   said optical radiation is split into two fractions;
   one said fraction is passed through a retained sample of the target gas and illuminates a first optical detector;
   the second said fraction is transmitted through said monitored space to illuminate a second optical detector in a receiver;
   a signal from the first optical detector is sent to said receiver as representative of the target gas.

66. Apparatus for detecting a target gas in a monitored space as claimed in claim 65 wherein:
   the signal from the first optical detector is used by the transmitter to maintain the conditions necessary for generation of the specific distortion 'fingerprint'; and
   the signal from said second optical detector is processed in relation to said specific distortion 'fingerprint' to calculate the quantity of target gas present in the monitored space and the receiver providing an output signal representative of the calculated quantity.

67. Apparatus for detecting a target gas in a monitored space as claimed in claim 66 wherein:
   an additional fraction of the optical radiation from the laser diode is sampled, this fraction directly illuminating an optical detector inside the transmitter;
   the signal from this detector is used to measure the magnitudes and phases of any 'fingerprint' components present in the waveform output by the laser diode in the absence of absorption by target gas; and
   this information is continuously communicated to the receiver to be subtracted from its measurements of the waveform of optical radiation that has been transmitted through the monitored space.

68. Apparatus for detecting a target gas in a monitored space as claimed in claim 66 wherein:
   the laser diode in the transmitter sequentially scans a total of two or more chosen absorption lines of one or more target gases and
   the retained gas sample includes a quantity of each of the one or more target gases and is used to maintain the conditions necessary for generation of specific distortion 'fingerprints' for each chosen absorption line of the one or more target gases.

69. Apparatus for detecting a target gas in a monitored space as claimed in claim 66 wherein:
   two or more laser diodes are used to detect or measure one or more target gases;
   the output from each laser diode is split into two fractions, one fraction used to illuminate a retained sample of the one or more target gases to maintain the conditions necessary for generation of specific distortion 'fingerprints' for each chosen absorption line of the one or more target gases, and the second fraction being transmitted through a monitored space to a receiver;
   the receiver is capable of detecting and processing the optical signals from the two or more laser diodes to calculate the quantities of the one or more target gases in the monitored space, this processing making use of the known, specific distortion 'fingerprints' which are being actively maintained by the transmitter.

70. Apparatus for detecting a target gas in a monitored space as claimed in claim 69 wherein:
   additional fractions of the optical radiation outputs from the laser diodes are sampled, which fractions directly illuminate an optical detector inside the transmitter;
   a signal from this detector is used to measure the magnitudes and phases of any 'fingerprint' components present in the waveforms output by the laser diodes in the absence of absorption by target gas; and
   this information is continuously communicated to the receiver to be subtracted from its measurements of the waveforms of optical radiation that has been transmitted through the monitored space.

71. Apparatus for detecting a target gas in a monitored space as claimed in claim 66 wherein the transmitter and the receiver are physically part of a single gas detection or measurement apparatus in which gas is drawn or diffuses into a sample measurement chamber in order to be illuminated by laser diode radiation and measured, the calculated gas quantity being output by the apparatus.

72. Apparatus for detecting a target gas in a monitored space as claimed in claim 66 wherein the means of output for the quantity of gas calculated present in the monitored space or sample measurement chamber includes:
   an analogue electrical signal proportional to the quantity of gas;
   a digital electronic signal conforming to a defined protocol and containing numerical information conveying the quantity of gas;
   a numerical representation of the quantity of gas upon a display which is associated with or forms part of the apparatus, or the opening or closing of relays at prescribed concentrations or quantities of gas, such relays and the necessary control circuitry either being associated with or forming part of the apparatus.

73. Apparatus for detecting a target gas in a monitored space, which apparatus comprises two or more laser diodes, wherein:
   each laser diode is being driven by a bias current which causes it to operate at a mean wavelength close to a different optical absorption line of the same target gas and is scanned across this line by a sinusoidal current component at a frequency which is non-harmonically related to any other scanning frequency used;
   the optical radiation from all said laser diodes being collected and transmitted through the monitored space and subsequently illuminating one or more optical detectors;
   an electrical signal from the detector or detectors is amplified, digitized and processed to determine the magnitude of components at the fundamental scanning frequencies and similar order harmonics of these fundamental frequencies;
   each harmonic is normalized with respect to the magnitude of its fundamental;

separate estimates of the quantity of target gas present in the monitored space are calculated based upon each normalized harmonic;

these quantity estimates are compared with each other and previous results for measurements made through the monitored space; and rules are applied dependent upon this quality, use of these quantities in combination with previous results to calculate the quantity of target gas present in the monitored space, the calculated quantity of gas being output by the apparatus.

74. Apparatus for detecting a target gas in a monitored space as claimed in claim 73 wherein the laser diodes are located in positions calculated to minimize formation of coherent interference fringes with common phase, amplitude or frequency.

75. Apparatus for detecting a target gas in a monitored space as claimed in claim 73 wherein the radiation from each laser diode is collected and collimated by separate optical elements with different, non-harmonically related effective focal lengths and thicknesses.

76. Apparatus for detecting a target gas in a monitored space as claimed in claim 73 wherein three mean wavelengths close to three distinct optical absorption lines of the same target gas are chosen such that:
  (a) all are in regions of low absorption by atmospheric gases; or
  (b) two are in regions of low absorption by atmospheric gases while the other is in a region of higher absorption by atmospheric gases; or
  (c) one is in a region of low absorption by atmospheric gases while the others are in regions of higher absorption by atmospheric gases; or
  (d) all are in regions affected by absorption by different atmospheric gas species or combinations thereof.

77. Apparatus for detecting a target gas in a monitored space as claimed in claim 73 wherein the rules governing the use of three estimated gas quantities $Q_1$, $Q_2$ and $Q_3$ in combination with results for previous measurements made through the monitored space to calculate the quantity of gas present in the monitored space are such that:
  (a) if $Q_1$, $Q_2$ and $Q_3$ are in close agreement, a large fraction of the average of $Q_1$, $Q_2$ and $Q_3$ is added to a balancing fraction of the running average of previous results; while
  (b) if either $Q_1$ and $Q_2$, or $Q_2$ and $Q_3$, or $Q_1$ and $Q_3$ are in close agreement with each other and the running average of previous results, the quantity which is not in close agreement is rejected while a large fraction of the average of the remaining quantities is added to a balancing fraction of the running average of previous results; while
  (c) if $Q_1$, $Q_2$ and $Q_3$ are in reasonable but not close agreement with each other and the running average of previous results, a lesser fraction of the average of $Q_1$, $Q_2$ and $Q_3$ is added to a larger balancing fraction of the running average of previous results; while
  (d) if $Q_1$, $Q_2$ and $Q_3$ are in reasonable but not close agreement with each other but not in close or reasonable agreement with the running average of previous results, a still lesser fraction of the average of $Q_1$, $Q_2$ and $Q_3$ is added to a still larger balancing fraction of the running average of previous results; while
  (e) if only one of the quantities $Q_1$, $Q_2$ or $Q_3$ is in close agreement with the running average of previous results, the other quantities are rejected and a fraction of the remaining quantity is added to a larger balancing fraction of the running average of previous results; while
  (f) if $Q_1$, $Q_2$ and $Q_3$ are in poor agreement with each other and the running average of previous results, $Q_1$, $Q_2$ and $Q_3$ are rejected and only the running average of previous results is used.

78. Apparatus for detecting a target gas in a monitored space as claimed in claim 73 wherein all the laser diodes are located closely together on a common temperature stabilized mount and have their outputs collimated by a common optical element.

79. Apparatus for detecting a target gas in a monitored space as claimed in claim 73 wherein the laser diodes and the laser diode bias currents are such that all the laser diodes are simultaneously operating at their correct mean wavelengths with near optimal output power while at a common temperature.

80. Apparatus for detecting a target gas in a monitored space as claimed in claim 73 wherein the wavelength scanning ranges for each laser diode are non-harmonically related and have significantly different characteristic distances with respect to the formation of coherent interference fringes.

81. Apparatus for detecting a target gas in a monitored space as claimed in claim 73 wherein:
  each target gas absorption line is scanned at two, non-harmonically related electrical frequencies and measurements of any absorption by such lines are made by determining the magnitude of the two, similar order harmonics of the non-harmonically related scanning frequencies; and wherein
  this process is carried out for each absorption line being scanned;
  and wherein this process is performed simultaneously, all electrical scanning frequencies being chosen to be non-harmonically related.

82. Apparatus for detecting a target gas in a monitored space as claimed in claim 73 wherein that the two mean wavelengths close to two separate optical absorption lines of the same target gas are chosen such that:
  (a) both are in regions of low absorption by atmospheric gases; or
  (b) one is in a region of low absorption by atmospheric gases while the other is in a region of higher absorption by atmospheric gases; or
  (c) one is in a region affected by absorption by one particular atmospheric gas species while the other is in a region affected by absorption by another atmospheric gas species.

83. Apparatus for detecting a target gas in a monitored space as claimed in claim 73 wherein the rules governing the use of two estimated gas quantities $Q_1$ and $Q_2$ in combination with results for previous measurements made through the monitored space to calculate the quantity of gas present in the monitored space are such that:
  (a) if $Q_1$ and $Q_2$ are in close agreement, a large fraction of the average of $Q_1$ and $Q_2$ is added to a balancing fraction of the running average of previous results; while
  (b) if $Q_1$ and $Q_2$ are in reasonable but not close agreement, a lesser fraction of the average of $Q_1$ and $Q_2$ is added to a larger balancing fraction of the running average of previous results; while
  (c) if only $Q_1$ or only $Q_2$ is in close or reasonable agreement with the running average of previous results, the quantity which is not in close or reasonable agreement is rejected while a lesser fraction of the close or reasonably agreeing quantity is added to a larger balancing fraction of the running average of previous results; while (d) if $Q_1$ and $Q_2$ are in poor agreement with each other and the running average of previous results, both $Q_1$ and $Q_2$ are rejected and only the running average of previous results is used.

84. Apparatus for detecting a target gas in a monitored space as claimed in claim 73 wherein the results of measurements performed upon target gas lines in regions of known low absorption by atmospheric gases are used to discriminate the effects of absorption by atmospheric gases in regions of more significant absorption by atmospheric gases from genuine changes in target gas concentration, thereby enabling any offsets arising from such absorption to be compensated for.

85. Apparatus for detecting a target gas in a monitored space as claimed in claim 73 wherein the diode lasers are VCSELs.

86. Apparatus for detecting a target gas in a monitored space as claimed in claim 73 wherein the means of collecting the laser radiation and transmitting it through the monitored space includes combinations of free-space optical elements and fiber-optics.

87. Apparatus for detecting a target gas in a monitored space as claimed in claim 73 wherein instead of amplifying, digitizing and digitally processing the detector signal(s) to determine the magnitudes of the various frequency components, the frequency component magnitudes are determined by amplifying the detector signal(s) and synchronously detecting the various frequency components using multiple synchronous detectors operating in parallel upon the signal(s).

88. Apparatus for detecting a target gas in a monitored space as claimed in claim 73 wherein said gas is drawn into a sample measurement chamber in which it is illuminated by the laser diode radiation.

89. Apparatus for detecting a target gas in a monitored space as claimed in claim 73 wherein said apparatus is arranged to detect hydrogen sulphide by measurement of any combination of two or more of the hydrogen sulphide absorption lines at 1582.13 nm, 1589.24 nm, 1589.42 nm, 1589.54 nm, 1589.97 nm and 1593.05 nm.

90. Apparatus for detecting a target gas in a monitored space as claimed in claim 73 wherein the means of output for the concentration or quantity of gas calculated present in the monitored path or sample measurement chamber includes:
   an analogue electrical signal proportional to the concentration or quantity of gas;
   a digital electronic signal conforming to a defined protocol and containing numerical information conveying the concentration or quantity of gas; and
   a numerical representation of the concentration or quantity of gas upon a display which is associated with or forms part of the apparatus, or the opening or closing of relays at prescribed concentrations or quantities of gas, such relays and the necessary control circuitry either being associated with or forming part of the apparatus.

91. A method of detecting a target gas in a monitored space comprising providing a tunable source of optical radiation, tuning said source so as to generate optical radiation of defined wavelength, transmitting the optical radiation of defined wavelength across the monitored space and determining the optical absorption thereof, wherein:
   said source is tuned to define two mean wavelengths $\Lambda_1$ and $\Lambda_2$ for the optical radiation with modulation at two frequencies f and f' respectively, where $\Lambda_1$ and $\Lambda_2$ are respectively close to two separate optical absorption lines of the target gas and f and f' are not harmonically related.

92. Apparatus for detecting a target gas in a monitored space, which apparatus comprises:
   a source of optical radiation tunable to generate optical radiation of defined wavelength and configured and arranged to transmit the optical radiation of defined wavelength radiation across the monitored space; and
   an optical receiver operable to receive the transmitted radiation and determine optical absorption thereof; wherein:
   said optical source is tuned to define two mean wavelengths $\Lambda_1$ and $\Lambda_2$ for the optical radiation with modulation at two frequencies f and f' respectively, where $\Lambda_1$ and $\Lambda_2$ are respectively close to two separate optical absorption lines of the target gas and f and f' are not harmonically related.

\* \* \* \* \*